(12) United States Patent
Zhang et al.

(10) Patent No.: US 10,479,791 B2
(45) Date of Patent: Nov. 19, 2019

(54) HETEROCYCLIC COMPOUNDS AS ERK INHIBITORS

(71) Applicants: CHANGZHOU JIEKAI PHARMATECH CO. LTD, Changzhou, Jiangsu (CN); JS INNOPHARM (SHANGHAI) LTD, Shanghai (CN)

(72) Inventors: Jintao Zhang, Naperville, IL (US); Wen Xu, Shanghai (CN); Shanzhong Jian, Shanghai (CN)

(73) Assignees: CHANGZHOU JIEKAI PHARMATECH CO. LTD, Changzhou, Jiangsu (CN); JS INNOPHARM (SHANGHAI) LTD, Shaghai (CN)

( * ) Notice: Subject to any disclaimer, the term of this patent is extended or adjusted under 35 U.S.C. 154(b) by 0 days.

(21) Appl. No.: 15/578,859

(22) PCT Filed: Jun. 3, 2015

(86) PCT No.: PCT/CN2015/080717
§ 371 (c)(1),
(2) Date: Dec. 1, 2017

(87) PCT Pub. No.: WO2016/192063
PCT Pub. Date: Dec. 8, 2016

(65) Prior Publication Data
US 2018/0179211 A1    Jun. 28, 2018

(51) Int. Cl.
*C07D 487/04* (2006.01)
*C07D 519/00* (2006.01)
*A61P 35/00* (2006.01)

(52) U.S. Cl.
CPC ............ *C07D 487/04* (2013.01); *A61P 35/00* (2018.01); *C07D 519/00* (2013.01)

(58) Field of Classification Search
CPC ...... A61P 35/00; C07D 487/04; C07D 519/00
See application file for complete search history.

(56) References Cited

FOREIGN PATENT DOCUMENTS

| WO | WO 2002064586 A2 | 8/2002 | |
|---|---|---|---|
| WO | WO 2005113546 A1 | 12/2005 | |
| WO | WO 2006058120 A1 | 6/2006 | |
| WO | WO 2013/130660 * | 9/2013 | ........... C07D 471/04 |
| WO | WO 2013130660 A1 | 9/2013 | |

OTHER PUBLICATIONS

Alex M. Aronov, Qing Tang, Gabriel Martinez-Botella, Guy W. Bemis, Jingrong Cao, Guanjing Chen, Nigel P. Ewing, Pamella J. Ford, Ursula A. Germann, Jeremy Green, Michael R. Hale, Marc Jacobs, James W. Janetka, Francois Maltais, William Markland, Mark N. Namchuk, Suganthini Nanthakumar, Srinivasu Poondru, Judy Straub, Ernst ter Haar and Xiaoling Xie. *Structure-guided design of potent and selective pyrimidylpyrrole inhibitors of extracellular signal-regulated kinase (ERK) using conformational control.* Journal of Medicinal Chemistry, Sep. 22, 2009, No. 20, vol. 52, pp. 6362-6368.

JS Sebolt-Leopold, R Herrera. *Targeting the mitogen-activated protein kinase cascade to treat cancer.* Nature Reviews Cancer. 2004. vol. 4, pp. 937-947.

W Kolch. *Coordinating ERK/MAPK signalling through scaffolds and inhibitors.* Nature Reviews Molecular Cell Biology. 2005. vol. 6, pp. 827-837.

S Yoon, R Seger. *The extracellular signalregulated kinase: Multiple substrates regulate diverse cellular functions.* Growth Factors. 2006. vol. 24, Issue 1, pp. 21-44.

AA Adjei. *Blocking oncogenic Ras signaling for cancer therapy.* Journal of the National Cancer Institute. 2001. vol. 93, Issue 14, pp. 1062-1074.

S Aviel-Ronen, FH Blackhall, FA Shepherd, MS Tsao. *K-ras Mutations in Non-Small-Cell Lung Carcinoma: A Review.* Clinical Lung Cancer. 2006. vol. 8, Issue 1, pp. 30-38.

NE Thomas. *BRAF somatic mutations in malignant melanoma and melanocytic naevi.* Melanoma Research. 2006. vol. 16, Issue 2, pp. 97-103.

G Singer, R Oldt III, Y Cohen, BG Wang, D Sidransky; RJ Kurman; IM Shih. *Mutations in BRAF and KRAS characterize the development of low-grade ovarian serous carcinoma.* Journal of the National Cancer Institute. 2003. vol. 95, Issue 6, pp. 484-486.

MS Brose, P Volpe, M Feldman, M Kumar, I Rishi, et al. *BRAF and RAS mutations in human lung cancer and melanoma.* Cancer Research. 2002. vol. 62, Issue 23, pp. 6997-7000.

JS Sebolt-Leopold. *Development of anticancer drugs targeting the MAP kinase pathway.* Oncogene. 2000. vol. 19, pp. 6594-6599.

R Mallon, L Feldberg, S Kim, K Collins, et al. *Identification of 4-anilino-3-quinolinecarbonitrile inhibitors of mitogen-activated protein/extracellular signal-regulated kinase 1 kinase.* Molecular Cancer. 2004. vol. 3, Issue 6, pp. 755-762.

(Continued)

*Primary Examiner* — Erich A Leeser
(74) *Attorney, Agent, or Firm* — Finnegan, Henderson, Farabow, Garrett & Dunner, LLP

(57) ABSTRACT

Disclosed herein is a compound of formula I and/or a pharmaceutically acceptable salt thereof that can serve as Erk inhibitors:

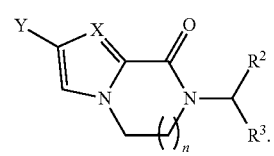

They are potentially useful in the treatment of diseases treatable by inhibition of Erk, such as cancers. Also disclosed herein is a pharmaceutical composition comprising a compound of formula I and/or a pharmaceutically acceptable salt thereof and a pharmaceutically acceptable carrier.

33 Claims, No Drawings

(56) References Cited

OTHER PUBLICATIONS

JS Sebolt-Leopold. *MEK inhibitors: a therapeutic approach to targeting the Ras-MAP kinase pathway in tumors*. Current Pharmaceutical Design. 2004. vol. 10, Issue 16, pp. 1907-1914.

EK Crane, KK Wong. *The Therapeutic Promise of Anti-Cancer Drugs Against the Ras/Raf/MEK/ERK Pathway*. Topics in Anti-Cancer Research. 2013. vol. 2, pp. 63-94.

International Search Report and Written Opinion for PCT Application No. PCT/CN2015/080717 dated Mar. 7, 2016.

* cited by examiner

HETEROCYCLIC COMPOUNDS AS ERK INHIBITORS

This application is a national stage filing under 35 U.S.C. § 371 of International Application No. PCT/CN2015/080717, filed on Jun. 3, 2015, the content of which is incorporated herein by reference.

Disclosed herein are novel heterocyclic compounds that can serve as extracellular signal-regulated kinases (ERK) inhibitors. Further disclosed herein are pharmaceutical compositions, comprising such compounds, as well as methods of using such compounds in treatment of diseases modulated by ERK, such as cancers.

The Ras-Raf-Mek-Erk intracellular signaling cascade is known as a central signaling module that transmits proliferation, survival, growth and differentiation signals into the cell interior from activated receptor tyrosine kinases (RTKs) such as ErbB family, PDGF, FGF, and VEGF (Sebolt-Leopold, J. S. and Herrera, R., *Nat. Rev. Cancer*, 41:937-947, 2004; Kolch, W., *Nat. Rev. Mol. Cell Biol.*, 61:827-837, 2005). This signaling axis includes Ras, Raf, Mek (mitogen-activated protein kinase kinase), and Erk (extracellular signal-regulated kinases) proteins all occurring in highly homologous isoforms. Ras proteins (e.g, H-Ras, N-Ras, and K-Ras) are 21 kDa GTPases that are activated at the proximity sites of the intracellular kinase domains of RTKs. Raf kinases (e.g, RafA, RafB, and RafC) are intermediate downstream effectors of Ras, activated by binding to GTP-loaded Ras. Raf kinases phosphorylate Meks (Mek1 and Mek2) on two closely adjacent serine residues, S218 and S222 in the case of Mek1. Meks are dual specificity theroine/tyrosine kinases that phosphorylate threonine and tyrosine residues within the TXY motif of Erks, where T represents threonine, Y represents tyrosine, and X represents any amino acid. Erk proteins (Erk1 and Erk2), also known as MAPKs (mitogen-activated proteins), are serine/threonine kinases that phosphorylate more than 100 downstream cytosolic and nuclear target proteins that participate in cellular processes such as division, proliferation, migration, and apoptosis (Yoon, S. and Seger, R., Growth Factors, 24:21-44, 2006). These phosphorylations substantially modulate, generally stimulate, the activity of the target proteins and can profoundly alter the physiological status of the cells.

Pathological activation of Ras-Raf-Mek-Erk cascade signaling pathway is known to account for the mechanistic aspects of most human cancers, immune dysfunction, and hyper-inflammatory conditions. Activation of the signaling pathway can occur as the result of autocrine or paracrine production of excessive RTK ligands, or constitutive activation of cell surface receptors by mutation or overexpression, or more commonly through gain-of-function mutations of B-Raf and Ras family members. Oncogenic forms of Ras are reported to be associated with 30% of all human cancers. Mutations in K-Ras occur in 90% of pancreatic and in 25% to 50% of colorectal, mucinous ovarian, and non-small cell lung cancers, whereas mutations in H-Ras are common in bladder, kidney, and thyroid cancers and N-Ras mutations are found in melanoma, hepatocellular carcinoma, and hematologic malignancies (Adjei, A., J Natl Cancer Inst, 93:1062-74, 2001; Aviel-Ronen, S., et al, Clin Lung Cancer, 8:30-8, 2006). B-Raf mutations occur in 66% to 70% of malignant melanomas, 70% of nonpapillary thyroid cancers, 35% of low-grade ovarian serous tumors as well as a wide range of other cancers including, for example, colorectal, thyroid, lung, breast, and ovarian cancers (Thomas, N., Melanoma Res, 16:97-103, 2006; Singer, G., et al, J Natl Cancer Inst, 95:484-6, 2003; Brose, M., et al, Cancer Res, 62:6997-7000, 2002).

Inhibition of the activity of Ras-Raf-Mek-Erk signaling pathway has been the focus of drug discovery, particularly for cancer treatment (Sebolt-Leopold, J., Oncogene, 19:16564-6599, 2000). Small-molecule inhibitors of B-Raf and Mek have been shown to effectively inhibit Ras and Raf mediated cell transformation, Erk activation and dependent processes, cell proliferation in vitro, tumor growth in vivo (Mallon, R., et al., Mol Cancer Ther, 31:755-762, 2004; Sebolt-Leopold, J., Curr Pharm Des, 101:1907-1914, 2004; Sebolt-Leopold J. and Herrera, R., Nat Rev Cancer, 41:937-947, 2004). The demonstration of the clinical efficacy of multiple Raf and Mek small-molecule inhibitors in various types of cancers has provided an ultimate validation of targeting this signaling pathway for cancer treatment (Crane, E. and Wang, K., Topics Anti-Cancer Res, 2:63-94, 2013).

Given Erk proteins' downstream position in the Ras-Raf-Mek-Erk signaling cascade, inhibition of Erks can provide an alternative strategy to modulate down the activity of the pathway. As such, there is a strong rationale to develop Erk small-molecule inhibitors as novel therapeutic agents for a broad spectrum of human cancers originated, for example, from brain, lung, colon, breast, gastric, pancreatic, head and neck, esophageal, renal, kidney, ovarian, skin, prostate, testicular, gynecological or thyroid. In addition, the Erk inhibitors may also be used to treat, for example, non-cancerous hyper-proliferative disorders (e.g., benign hyperplasia of the skin, restenosis, benign prostatic hypertrophy), pancreatitis, kidney disease, pain, diseases related to vasculogenesis or angiogenesis, acute and chronic inflammatory disease (e.g., rheumatoid arthritis, athero sclerosis, inflammatory bowel disease), skin diseases (e.g., psoriasis, eczema, and scleroderma), diabetes, diabetic retinopathy, retinopathy of prematurity, age-related macular degeneration, asthma, septic shock, T-cell mediated diseases, chronic obstructive pulmonary disease (COPD).

Disclosed herein is a compound of formula I:

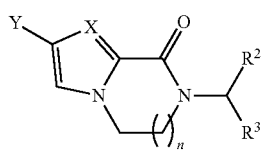

and/or a pharmaceutically acceptable salt thereof;
wherein:

X is N or C—R, wherein R is hydrogen, halo, alkyl, haloalkyl, —CN, or alkoxy;

Y is aryl or heteroaryl optionally substituted with at least one group selected from halo, alkyl, alkenyl, alkoxy, alkynyl, aryl, cycloalkyl, heteroaryl, heterocyclyl, —OH, —CN, —COOR$_a$, —SO$_2$NR$_a$R$_b$, —CONR$_a$R$_b$, and —NR$_a$R$_b$, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONR$_a$R$_b$, and —NR$_a$R$_b$;

R$^2$ is hydrogen, aryl, —CONR$_a$R$_b$, alkyl, alkoxy, —COOR$_a$, cycloalkyl, heteroaryl, or heterocyclyl;

R$^3$ is hydrogen, alkyl, aryl, cycloalkyl, alkenyl, alkynyl, alkoxy, heteroaryl, or heterocyclyl;

wherein each of the alkyl, alkoxy, aryl, cycloalkyl, alkenyl, alkynyl, heteroaryl, and heterocyclyl for $R^2$ and/or $R^3$ is optionally substituted with at least one group selected from —OH, alkoxy, halo, and alkyl;

$R_a$ and $R_b$ are independently hydrogen, alkyl, aryl, cycloalkyl, heterocyclyl, or heteroaryl, wherein each of the alkyl, aryl, cycloalkyl, heterocyclyl, and heteroaryl is optionally substituted with at least one group selected from halo, alkyl, haloalkyl, alkoxy, —C(O)-alkyl, —SO$_2$-alkyl, —OH, cycloalkyl, and heterocyclyl optionally substituted with at least one group selected from alkyl, —C(O)-alkyl, and —SO$_2$-alkyl; or $R_a$ and $R_b$, together with the atoms to which they are attached, form a heterocyclic ring optionally substituted with at least one group selected from halo, alkyl, haloalkyl, alkoxy, and —OH; and n is 1, 2, or 3.

Also disclosed herein is a pharmaceutical composition, comprising a compound of formula I and/or a pharmaceutically acceptable salt thereof disclosed herein and a pharmaceutically acceptable carrier.

Further disclosed herein is a method of inhibiting the activity of Erk comprising contacting the protein Erk with an effective amount of a compound of formula I and/or a pharmaceutically acceptable salt thereof disclosed herein.

Further disclosed herein is a method of treating a disease treatable by inhibition of Erk in a patient, comprising administering to the patient in recognized need of such treatment, an effective amount of a compound of formula I and/or a pharmaceutically acceptable salt thereof disclosed herein.

Further disclosed herein is a method of treating a disease treatable by inhibition of Erk in a patient, comprising administering to the patient in recognized need of such treatment, an effective amount of a pharmaceutical composition comprising a compound of formula I and/or a pharmaceutically acceptable salt thereof disclosed herein and a pharmaceutically acceptable carrier.

Further disclosed herein is a use of a compound of formula I and/or a pharmaceutically acceptable salt thereof in preparation of a medication for treating a disease responsive to inhibition of Erk.

The diseases treatable by inhibition of Erk include, for example, cancers and inflammatory diseases, and skin diseases. Further exemplary diseases include colon cancer, gastric cancer, leukemia, lymphoma, melanoma, pancreate cancer, rheumatoid arthritis, psoriasis, and eczema.

As used herein, the following words, phrases and symbols are generally intended to have the meanings as set forth below, except to the extent that the context in which they are used indicates otherwise. The following abbreviations and terms have the indicated meanings throughout.

Further disclosed herein is a method of treating at least one disease selected from inflammatory diseases and cancers in a patient, comprising administering to the patient in recognized need of such treatment, an effective amount of a pharmaceutical composition comprising a compound of formula I and/or a pharmaceutically acceptable salt thereof disclosed herein and a pharmaceutically acceptable carrier. Exemplary cancers include colon cancer, gastric cancer, leukemia, lymphoma, melanoma, and pancreate cancer. Exemplary inflammatory diseases include rheumatoid arthritis, psoriasis, and eczema.

A dash ("-") that is not between two letters or symbols is used to indicate a point of attachment for a substituent. For example, —CONR$_a$R$_b$ is attached through the carbon atom.

Unless clearly indicated otherwise, use of the terms "a", "an" and the like refers to one or more.

The term "alkyl" herein refers to a hydrocarbon group selected from linear and branched saturated hydrocarbon groups comprising from 1 to 18 carbon atoms, such as from 1 to 12, further such as from 1 to 10, even further such as from 1 to 6, carbon atoms.

The term "alkoxy" herein refers to a straight or branched alkyl group comprising from 1 to 10 carbon atoms attached through an oxygen bridge such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. In some embodiments, alkoxy groups comprise from 1 to 6 carbon atoms attached through the oxygen bridge.

The term "alkenyl" herein refers to a hydrocarbon group selected from linear and branched hydrocarbon groups, comprising at least one C=C double bond and from 2 to 18, such as from 2 to 6, carbon atoms. Examples of the alkenyl group may be selected from ethenyl or vinyl (—CH=CH$_2$), prop-1-enyl (—CH=CHCH$_3$), prop-2-enyl (—CH$_2$CH=CH$_2$), 2-methylprop-1-enyl, buta-1-enyl, buta-2-enyl, buta-3-enyl, buta-1,3-dienyl, 2-methylbuta-1,3-diene, hex-1-enyl, hex-2-enyl, hex-3-enyl, hex-4-enyl, and hexa-1,3-dienyl groups. The point of attachment can be on the unsaturated carbon or saturated carbon.

The term "alkynyl" herein refers to a hydrocarbon group selected from linear and branched hydrocarbon groups, comprising at least one C≡C triple bond and from 2 to 18, such as from 2 to 6, carbon atoms. Examples of the alkynyl group include ethynyl (—C≡CH), 1-propynyl (—C≡CCH$_3$), 2-propynyl (propargyl, —CH$_2$C≡CH), 1-butynyl, 2-butynyl, and 3-butynyl groups. The point of attachment can be on the unsaturated carbon or saturated carbon.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12 carbon atoms, such as from 3 to 8, further such as from 3 to 6, from 3 to 5, or from 3 to 4, carbon atoms. Even further for example, the cycloalkyl group may be selected from monocyclic group comprising from 3 to 12 carbon atoms, such as from 3 to 8, or from 3 to 6, carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those comprising from 7 to 12 ring atoms arranged as a bicycle ring selected from [4,4], [4,5], [5,5], [5,6] and [6,6] ring systems, or as a bridged bicyclic ring selected from, for example, bicyclo[2.2.1] heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein. The cycloalkyl may be substituted with at least one hetero atom selected, for example, from O, S, and N.

The term "aryl" herein refers to a group selected from:
5- and 6-membered carbocyclic aromatic rings, for example, phenyl;
bicyclic ring systems such as 7 to 12 membered bicyclic ring systems wherein at least one ring is carbocyclic and aromatic, selected, for example, from naphthalene, indane, and 1,2,3,4-tetrahydroquinoline; and tricyclic ring systems such as 10 to 15 membered tricyclic ring systems, wherein at least one ring is carbocyclic and aromatic, for example, fluorene.

In some embodiments, the aryl group is selected from 5 and 6-membered carbocyclic aromatic rings fused to a 5- to 7-membered cycloalkyl or heterocyclic ring (as defined in "heterocyclyl" or "heterocyclic" below) optionally comprising at least one heteroatom selected, for example, from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring (e.g., a heteroaryl as defined below), the resulting ring system is heteroaryl, not aryl, as defined herein.

The term ""halo" herein refers to F, Cl, Br or I.

The term "heteroaryl" herein refers to a group selected from:
- 5- to 7-membered aromatic, monocyclic rings comprising at least one heteroatom, for example, from 1 to 4, or, in some embodiments, from 1 to 3, heteroatoms, selected, for example, from N, O, and S, with the remaining ring atoms being carbon;
- 8- to 12-membered bicyclic rings comprising at least one heteroatom, for example, from 1 to 4, or, in some embodiments, from 1 to 3, or, in other embodiments, 1 or 2, heteroatoms, selected, for example, from N, O, and S, with the remaining ring atoms being carbon and wherein at least one ring is aromatic and at least one heteroatom is present in the aromatic ring, and with the point of attachment being on any ring and being on either carbon or the heteroatom; and
- 11- to 14-membered tricyclic rings comprising at least one heteroatom, for example, from 1 to 4, or in some embodiments, from 1 to 3, or, in other embodiments, 1 or 2, heteroatoms, selected, for example, from N, O, and S, with the remaining ring atoms being carbon and wherein at least one ring is aromatic and at least one heteroatom is present in an aromatic ring, and with the point of attachment being on any ring.

In some embodiments, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

In some embodiments, the heteroaryl group includes a 5- to 7-membered heterocyclic aromatic ring fused to a 5- to 7-membered aryl ring. For such fused, bicyclic heteroaryl ring systems wherein only one of the rings comprises at least one heteroatom, the point of attachment may be at the heteroaromatic ring or at the aryl ring. Non-limiting examples include quinolinyl and quinazolinyl.

In some embodiments, the heteroaryl group includes a 5- to 7-membered heterocyclic aromatic ring fused to another 5- to 7-membered heterocyclic aromatic ring. Non-limiting examples include 1H-pyrazolo[3,4-b]pyridinyl and 1H-pyrrolo[2,3-b]pyridinyl.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, pyridyl, cinnolinyl, pyrazinyl, pyrimidinyl, imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-3-yl), pyrazolopyridinyl (such as 1H-pyrazolo[3,4-b]pyridin-3-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclyl" or "heterocyclic" herein refers to a ring selected from 4- to 12-membered monocyclic, bicyclic and tricyclic, saturated and partially unsaturated rings comprising at least one carbon atom in addition to at least one heteroatom, such as from 1-4 heteroatoms, further such as from 1-3, or further such as 1 or 2, heteroatoms, selected, for example, from O, S, and N. The point of attachment of heterocyclyl can be on the heteroatom or carbon. "Heterocyclyl" herein also refers to a 5- to 7-membered saturated or partially unsaturated carbocyclic ring comprising at least one heteroatom selected, for example, from N, O, and S (heterocyclic ring) fused with 5-, 6-, and/or 7-membered cycloalkyl, heterocyclic or carbocyclic aromatic ring, provided that the point of attachment is at the heterocyclic ring when the heterocyclic ring is fused with a carbocyclic aromatic ring, and that the point of attachment can be at the cycloalkyl or heterocyclic ring when the heterocylic ring is fused with cycloalkyl. "Heterocyclyl" herein also refers to an aliphatic spirocyclic ring comprising at least one heteroatom selected, for example, from N, O, and S. The rings may be saturated or have at least one double bond (i.e. partially unsaturated). The heterocyclyl may be substituted with, for example, oxo. The point of the attachment may be carbon or heteroatom. A heterocyclyl is not a heteroaryl as defined herein.

Examples of the heterocycle include, but not limited to, pyrrolidinyl, imidazolidinyl, pyrazolidinyl, piperidinyl, piperidinyl, piperazinyl, pyranyl, morpholinyl, oxiranyl, aziridinyl, thiiranyl, azetidinyl, oxetanyl, thietanyl, dithietanyl, dihydropyridinyl, tetrahydropyridinyl, thiomorpholinyl, thioxanyl, homopiperazinyl, homopiperidinyl, azepanyl, oxepanyl, thiepanyl, oxathianyl, dioxepanyl, oxathiepanyl, oxaazepanyldithiepanyl, thiazepanyl and diazepane, dithianyl, azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, indolinyl, dioxanyl, pyrazolinyl, dithianyl, dithiolanyl, pyrazolidinylimidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Substituted heterocycles also include ring systems substituted with one or more oxo moieties, such as piperidinyl N-oxide, morpholinyl-N-oxide, 1-oxo-1-thiomorpholinyl and 1,1-dioxo-1-thiomorpholinyl.

Compounds disclosed herein may contain an asymmetric center and may thus exist as enantiomers. Where the compounds disclosed herein possess two or more asymmetric centers, they may additionally exist as diastereomers. Enantiomers and diastereomers fall within the broader class of stereoisomers. It is well-known in the art how to prepare optically active forms, such as by resolution of materials or by asymmetric synthesis. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

When the compounds disclosed herein contain olefinic double bonds, unless specified otherwise, such double bonds are meant to include both E and Z geometric isomers.

The term "optional" or "optionally" means that the subsequently described event or circumstance may or may not occur, and that the description includes instances where the event or circumstance occurs and instances in which it does not. For example, "alkyl optionally substituted with X" encompasses both "alkyl without substitution of X" and "alkyl substituted with X". It will be understood by those skilled in the art, with respect to any group containing one or more substituents, that such groups are not intended to introduce any substitution or substitution patterns that are sterically impractical, synthetically non-feasible and/or inherently unstable.

In some embodiments, "substituted with at least one group" refers to one hydrogen on the designated atom or group being replaced with one selection from the indicated group of substituents. In some embodiments, "substituted with at least one group" refers to two hydrogens on the designated atom or group being independently replaced with two selections from the indicated group of substituents. In some embodiments, "substituted with at least one group" refers to three hydrogens on the designated atom or group being independently replaced with three selections from the indicated group of substituents. In some embodiments, "substituted with at least one group" refers to four hydrogens on the designated atom or group being independently replaced with four selections from the indicated group of substituents.

"A pharmaceutically acceptable salt" includes, but is not limited to, salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—(CH$_2$)n-COOH, wherein n is selected from 0 to 4. Similarly, examples of pharmaceutically acceptable cations include, but are not limited to, sodium, potassium, calcium, aluminum, lithium, and ammonium.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" or "alleviation" refers to administering at least one compound and/or at least one stereoisomer thereof, if any, and/or at least one pharmaceutically acceptable salt thereof disclosed herein to a subject in recognized need thereof that has, for example, cancer.

The term "effective amount" refers to an amount of at least one compound and/or at least one stereoisomer thereof, if any, and/or at least one pharmaceutically acceptable salt thereof disclosed herein effective to "treat," as defined above, a disease or disorder in a subject.

Formula I

Disclosed herein is a compound of formula I:

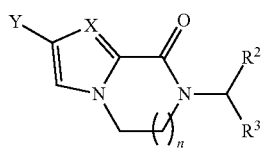

and/or a pharmaceutically acceptable salt thereof;
wherein:
X is N or C—R, wherein R is H, halo, alkyl, haloalkyl, —CN, or alkoxy;
Y is aryl or heteroaryl optionally substituted with at least one group selected from halo, alkyl, alkenyl, alkoxy, alkynyl, aryl, cycloalkyl, heteroaryl, heterocyclyl, —OH, —CN, —COOR$_a$, —SO$_2$NR$_a$R$_b$, —CONR$_a$R$_b$, and —NR$_a$R$_b$, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONR$_a$R$_b$, and —NR$_a$R$_b$;
R$^2$ is hydrogen, aryl, —CONR$_a$R$_b$, alkyl, alkoxy, —COOR$_a$, cycloalkyl, heteroaryl, or heterocyclyl;
R$^3$ is hydrogen, alkyl, aryl, cycloalkyl, alkenyl, alkynyl, alkoxy, heteroaryl, or heterocyclyl;
wherein each of the alkyl, alkoxy, aryl, cycloalkyl, alkenyl, alkynyl, heteroaryl, and heterocyclyl for R$^2$ and/or R$^3$ is optionally substituted with at least one group selected from —OH, alkoxy, halo, and alkyl;
R$_a$ and R$_b$ are independently H, alkyl, aryl, cycloalkyl, heterocyclyl, or heteroaryl, wherein each of the alkyl, aryl, cycloalkyl, heterocyclyl, and heteroaryl is optionally substituted with at least one group selected from halo, alkyl, haloalkyl, alkoxy, —C(O)-alkyl, —SO$_2$-alkyl, —OH, cycloalkyl, and heterocyclyl optionally substituted with at least one group selected from alkyl, —C(O)-alkyl, and —SO$_2$-alkyl; or
R$_a$ and R$_b$, together with the atoms to which they are attached, form a heterocyclic ring optionally substituted with at least one group selected from halo, alkyl, haloalkyl, alkoxy, and —OH; and
n is 1, 2, or 3.

In some embodiments, X is N. In some embodiments, X is C—R, wherein R is H, halo, alkyl, haloalkyl, —CN, or alkoxy. In some embodiments, X is C—R, wherein R is H, alkyl, haloalkyl, or alkoxy. In some embodiments, X is C—R, wherein R is H or alkly. In some embodiments, X is C—R, wherein R is H.

In some embodiments, Y is aryl optionally substituted with at least one group selected from halo, alkyl, alkenyl, alkoxy, alkynyl, aryl, cycloalkyl, heteroaryl, heterocyclyl, —OH, —CN, —COOR$_a$, —SO$_2$NR$_a$R$_b$, —CONR$_a$R$_b$, and —NR$_a$R$_b$, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONR$_a$R$_b$, and —NR$_a$R$_b$, and wherein R$_a$ and R$_b$ are as defined above.

In some embodiments, Y is a fused bicyclic aryl, such as 1H-indenyl or 1,2-dihydronaphthalene, optionally substituted with at least one group selected from halo, alkyl, alkenyl, alkoxy, alkynyl, aryl, cycloalkyl, heteroaryl, heterocyclyl, —OH, —CN, —COOR$_a$, —SO$_2$NR$_a$R$_b$, —CONR$_a$R$_b$, and —NR$_a$R$_b$, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONRaRb, and —NRaRb, and wherein Ra and Rb are as defined above.

In some embodiments, Y is a indenyl or 1,2-dihydronaphthalene substituted with an aryl or heteroaryl, wherein the aryl or heteroaryl is optionally substituted with at least one group selected from alkoxy, alkyl, halo, OH, —CN, —COOR$_a$, —SO$_2$NR$_a$R$_b$, —CONRaRb, and —NRaRb, and wherein Ra and Rb are as defined above. In some embodiments, Y is a indenyl or 1,2-dihydronaphthalene substituted with an aryl, such as phenyl.

In some embodiments, Y is a heteroaryl optionally substituted with at least one group selected from halo, alkyl, alkenyl, alkoxy, alkynyl, aryl, cycloalkyl, heteroaryl, heterocyclyl, —OH, —CN, —COORa, —SO2NRaRb, —CONRaRb, and —NRaRb, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONR$_a$R$_b$, and —NR$_a$R$_b$, and wherein R and R$_b$ are as defined above.

In some embodiments, Y is 1H-pyrazolo[3,4-b]pyridinyl, 1H-pyrrolo[2,3-b]pyridinyl, or pyrimidinyl optionally substituted with at least one group selected from halo, alkyl, alkenyl, alkoxy, alkynyl, aryl, cycloalkyl, heteroaryl, heterocyclyl, —OH, —CN, —COORa, —SO2NRaRb, —CONRaRb, and —NRaRb, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONRaRb, and —NRaRb, and wherein Ra and Rb are as defined above.

In some embodiments, Y is 1H-pyrazolo[3,4-b]pyridinyl or 1H-pyrrolo[2,3-b]pyridinyl optionally substituted with at least one group selected from halo, alkyl, alkenyl, alkoxy, alkynyl, aryl, cycloalkyl, heteroaryl, heterocyclyl, —OH, —CN, —COORa, —SO2NRaRb, —CONRaRb, and —NRaRb, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONRaRb, and —NRaRb, and wherein Ra and Rb are as defined above.

In some embodiments, Y is 1H-pyrazolo[3,4-b]pyridinyl or 1H-pyrrolo[2,3-b]pyridinyl optionally substituted with at least one group selected from alkyl, aryl, cycloalkyl, heteroaryl, and heterocyclyl, wherein each of the alkyl, aryl, cycloalkyl, heteroaryl, and heterocyclyl is optionally substituted with at least one group selected from alkoxy, alkyl, halo, OH, —CN, —COOR$_a$, —SO$_2$NR$_a$R$_b$, —CONRaRb, and —NRaRb, and wherein Ra and Rb are as defined above.

In some embodiments, Y is 1H-pyrazolo[3,4-b]pyridinyl or 1H-pyrrolo[2,3-b]pyridinyl substituted with aryl or heteroaryl, wherein each of the aryl and heteroaryl is optionally substituted with at least one group selected from alkoxy, alkyl, halo, OH, —CN, —COOR$_a$, —SO$_2$NR$_a$R$_b$, —CONRaRb, and —NRaRb, and wherein Ra and Rb are as defined above.

In some embodiments, Y is 1H-pyrazolo[3,4-b]pyridinyl or 1H-pyrrolo[2,3-b]pyridinyl substituted with aryl, wherein the aryl is optionally substituted with at least one group selected from alkoxy, alkyl, halo, OH, —CN, —COOR$_a$, —SO$_2$NR$_a$R$_b$, —CONRaRb, and —NRaRb, and wherein Ra and Rb are as defined above.

In some embodiments, Y is 1H-pyrazolo[3,4-b]pyridinyl or 1H-pyrrolo[2,3-b]pyridinyl substituted with phenyl, wherein the phenyl is optionally substituted with at least one group selected from alkoxy, alkyl, halo, OH, —CN, —COOR$_a$, —SO$_2$NR$_a$R$_b$, —CONRaRb, and —NRaRb, and wherein Ra and Rb are as defined above.

In some embodiments, Y is pyrimidinyl optionally substituted with at least one group selected from halo, alkyl, alkenyl, alkoxy, alkynyl, aryl, cycloalkyl, heteroaryl, heterocyclyl, —OH, —CN, —COORa, —SO2NRaRb, —CONRaRb, and —NRaRb, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONRaRb, and —NRaRb, and wherein Ra and Rb are as defined above.

In some embodiments, Y is pyrimidinyl substituted with at least one group selected from halo, alkyl, alkenyl, alkoxy, alkynyl, aryl, cycloalkyl, heteroaryl, heterocyclyl, —OH, —CN, —COORa, —SO2NRaRb, —CONRaRb, and —NRaRb, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONRaRb, and —NRaRb, and wherein Ra and Rb are as defined above.

In some embodiments, Y is pyrimidinyl substituted with at least one group selected from alkyl and —NRaRb, wherein the alkyl is optionally substituted with at least one group selected from alkoxy, alkyl, halo, OH, —CN, —COOR$_a$, —SO$_2$NR$_a$R$_b$, —CONRaRb, and —NRaRb, and wherein Ra and Rb are as defined above.

In some embodiments, Y is pyrimidinyl substituted with at least one group selected from alkyl and —NRaRb, wherein Ra and Rb are independently H, alkyl, aryl, or heteroaryl, wherein each of the alkyl, aryl, and heteroaryl for Ra and Rb is optionally substituted with at least one group selected from halo, alkyl, haloalkyl, alkoxy, —OH, and heterocyclyl optionally substituted with at least one group selected from alkyl, —C(O)-alkyl, and —SO2-alkyl.

In some embodiments, Y is pyrimidinyl substituted with two groups independently selected from alkyl and —NRaRb, wherein Ra and Rb are independently H or aryl (such as phenyl), wherein the aryl (such as phenyl) is optionally substituted with at least one group selected from halo, alkyl, haloalkyl, alkoxy, —OH, and heterocyclyl optionally substituted with at least one group selected from alkyl, —C(O)-alkyl, and —SO2-alkyl.

In some embodiments, Y is pyrimidinyl substituted with two groups independently selected from alkyl and —NRaRb, wherein Ra and Rb are independently H or aryl (such as phenyl), wherein the aryl (such as phenyl) is optionally substituted with at least one group selected from halo, alkyl, haloalkyl, alkoxy, —OH, and heterocyclyl optionally substituted with at least one group selected from alkyl, —C(O)-alkyl, and —SO2-alkyl.

In some embodiments, Y is pyrimidinyl substituted with two groups independently selected from alkyl and —NRaRb, wherein Ra and Rb are independently H or phenyl, wherein the phenyl is optionally substituted with at least one group selected from halo, alkyl, and heterocyclyl optionally substituted with at least one group selected from alkyl, —C(O)-alkyl, and —SO2-alkyl.

In some embodiments, $R^2$ is aryl, cycloalkyl, heteroaryl, or heterocyclyl, wherein each of the aryl, cycloalkyl, heteroaryl, and heterocyclyl is optionally substituted with at least one group selected from —OH, alkoxy, halo, and alkyl.

In some embodiments, $R^2$ is aryl or heteroaryl, wherein each of the aryl, cycloalkyl, heteroaryl, and heterocyclyl is optionally substituted with at least one group selected from —OH, alkoxy, halo, and alkyl.

In some embodiments, $R^2$ is aryl, wherein the aryl is optionally substituted with at least one group selected from —OH, alkoxy, halo, and alkyl.

In some embodiments, $R^2$ is phenyl substituted with at least one group selected from —OH, alkoxy, halo, and alkyl.

In some embodiments, $R^3$ is alkyl, aryl, or heteroaryl, wherein each of the alkyl, aryl, and heteroaryl is optionally substituted with at least one group selected from —OH, alkoxy, halo, and alkyl.

In some embodiments, $R^3$ is alkyl or heteroaryl, wherein each of the alkyl and heteroaryl is optionally substituted with at least one group selected from —OH, alkoxy, halo, and alkyl. In some embodiments, $R^3$ is an alkyl, such as methyl, optionally substituted with at least one group selected from —OH, alkoxy, and halo. In some embodiments, $R^3$ is hydroxymethyl. In some embodiments, $R^3$ is pyrazolyl substituted with an alkyl, such as methyl.

In some embodiments, the carbon to which R2 and R3 are attached has the following chiral orientation:

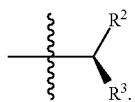

In some embodiments, the carbon to which R2 and R3 are attached has the following chiral orientation:

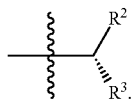

In some embodiments, n is 1. In some embodiments, n is 2. In some embodiments, n is 3.

Formula II

In some embodiments, the compound of formula I and/or a pharmaceutically acceptable salt thereof is a compound of formula II and/or a pharmaceutically acceptable salt thereof:

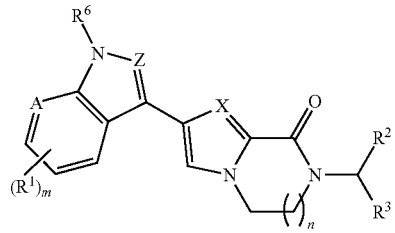

wherein:

$X$, $R^2$ and $R^3$ are as defined in formula I;

$Z$ is N or C—$R^5$, wherein $R^5$ is H or alkyl optionally substituted with at least one group selected from alkoxy and halo;

$R^6$ is H or alkyl optionally substituted with at least one group selected from alkoxy and halo;

A is N or C—$R^7$, wherein $R^7$ is H or alkyl optionally substituted with at least one group selected from alkoxy and halo;

m is 1 or 2;

n is 1, 2, or 3;

$R^1$ is independently halo, alkyl, alkenyl, alkoxy, alkynyl, aryl, cycloalkyl, heteroaryl, heterocyclyl, —OH, —CN, —COOR$_a$, —SO2NR$_a$R$_b$, —CONR$_a$R$_b$, or —NR$_a$R$_b$, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONR$_a$R$_b$, and —NR$_a$R$_b$;

$R_a$ and $R_b$ are as defined for formula I.

In some embodiments of formula II, Z is N. In some embodiments of formula II, $R^6$ is H. In some embodiments, A is N. In some embodiments of formula II, X is C—R, wherein R is H or alkyl. In some embodiments of formula II, X is C—H.

In some embodiments of formula II, $R^1$ is independently aryl or cycloalkyl, each of which is optionally substituted with at least one group selected from alkyl and halo.

In some embodiments of formula II, $R^1$ is phenyl, which is optionally substituted with at least one group selected from alkyl and halo.

In some embodiments of formula II, the carbon to which $R^2$ and $R^3$ are attached has the following chiral orientation:

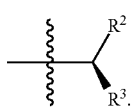

In some embodiments of formula II, $R^3$ is an alkyl optionally substituted with —OH. In some embodiments of formula II, $R^3$ is a heteroaryl, such as pyrazolyl optionally substituted with alkyl.

In some embodiments of formula II, $R^2$ is an aryl optionally substituted with at least one group selected from alkyl and halo. In some embodiments of formula II, $R^2$ is a phenyl optionally substituted with at least one group selected from alkyl and halo.

In some embodiments of formula II, n is 1. In some embodiments of formula II, n is 2.

Formula III

In some embodiments, the compound of formula I and/or a pharmaceutically acceptable salt thereof is a compound of formula III and/or a pharmaceutically acceptable salt thereof:

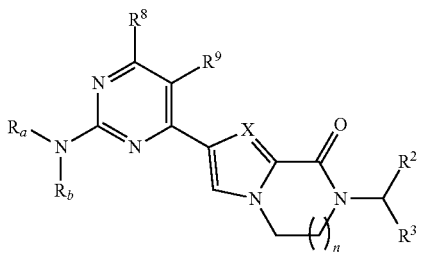

wherein:
X, R², and R³ are as defined in formula I;
R⁸ and R⁹ are independently H or alkyl optionally substituted with at least one group selected from alkoxy and halo;
n is 1, 2, or 3;
Rₐ and R_b are as defined in formula I.

In some embodiments of formula III, R⁸ is H and R⁹ is an alkyl, such as methyl.

In some embodiments of formula III, Ra is H, and Rb is cycloalkyl or heterocyclyl optionally substituted with at least one group selected from alkyl and —(SO)₂-alkyl.

In some embodiments of formula III, Ra is H, and Rb is an aryl, such as a phenyl, optionally substituted with at least one group selected from halo, alkyl, and heterocycyl optionally substituted with at least one group selected from alkyl, —C(O)-alkyl, and —(SO)₂-alkyl.

In some embodiments of formula III, X is C—H.

In some embodiments of formula III, the carbon to which R² and R³ are attached has the following chiral orientation:

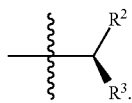

In some embodiments of formula III, R³ is an alkyl optionally substituted with —OH. In some embodiments, R³ is a heteroaryl, such as pyrazolyl optionally substituted with alkyl.

In some embodiments of formula III, R² is an aryl optionally substituted with one, two, or three groups independently selected from alkyl and halo. In some embodiments of formula III, R² is a phenyl optionally substituted with at least one group independently selected from alkyl and halo.

In some embodiments of formula III, n is 1. In some embodiments of formula III, n is 2.

In some embodiments, the compound of formula I is selected from
(S)-2-(1-(3-chloro-4-fluorophenyl)-2-hydroxyethyl)-7-(5-phenyl-1H-pyrazolo[3,4-b]pyridin-3-yl)-3,4-dihydropyrrolo[1,2-a]pyrazin-1 (2H)-one;
(R)-2-(1-(3-chloro-4-fluorophenyl)-2-hydroxyethyl)-7-(5-phenyl-1H-pyrazolo[3,4-b]pyridin-3-yl)-3,4-dihydropyrrolo[1,2-a]pyrazin-1(2H)-one;
a mixture of(S)- and (R)-2-(1-(3-chloro-4-fluorophenyl)-2-hydroxyethyl)-7-(5-phenyl-1H-pyrazolo[3,4-b]pyridin-3-yl)-3,4-dihydropyrrolo[1,2-a]pyrazin-(2H)-one;
(R)-2-(1-(3-chlorophenyl)ethyl)-7-(5-phenyl-1H-pyrrolo[2,3-b]pyridin-3-yl)-3,4-dihydropyrrolo[1,2-a]pyrazin-1(2H)-one;
(S)-2-(1-(3-chlorophenyl)ethyl)-7-(5-phenyl-1H-pyrrolo[2,3-b]pyridin-3-yl)-3,4-dihydropyrrolo[1,2-a]pyrazin-1(2H)-one;
a mixture of (R)- and (S)-2-(1-(3-chlorophenyl)ethyl)-7-(5-phenyl-1H-pyrrolo[2,3-b]pyridin-3-yl)-3,4-dihydropyrrolo[1,2-a]pyrazin-1 (2H)-one;
(R)-2-(1-(3-chlorophenyl)ethyl)-7-(5-phenyl-1H-pyrazolo[3,4-b]pyridin-3-yl)-3,4-dihydropyrrolo[1,2-a]pyrazin-1 (2H)-one;
(S)-2-(1-(3-chlorophenyl)ethyl)-7-(5-phenyl-1H-pyrazolo[3,4-b]pyridin-3-yl)-3,4-dihydropyrrolo[1,2-a]pyrazin-(2H)-one;
a mixture of (R)- and (S)-2-(1-(3-chlorophenyl)ethyl)-7-(5-phenyl-1H-pyrazolo[3,4-b]pyridin-3-yl)-3,4-dihydropyrrolo[1,2-a]pyrazin-1(2H)-one;
(S)-2-(1-(3-chlorophenyl)-2-hydroxyethyl)-7-(5-phenyl-1H-pyrrolo[2,3-b]pyridin-3-yl)-3,4-dihydropyrrolo[1,2-a]pyrazin-1(2H)-one;
(R)-2-(1-(3-chlorophenyl)-2-hydroxyethyl)-7-(5-phenyl-1H-pyrrolo[2,3-b]pyridin-3-yl)-3,4-dihydropyrrolo[1,2-a]pyrazin-1(2H)-one;
a mixture of (R)- and (S)-2-(1-(3-chlorophenyl)-2-hydroxyethyl)-7-(5-phenyl-1H-pyrrolo[2,3-b]pyridin-3-yl)-3,4-dihydropyrrolo[1,2-a]pyrazin-1(2H)-one;
(S)-7-(2-((2-chloro-4-fluorophenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(R)-7-(2-((2-chloro-4-fluorophenyl)amino)-5-methylpyrimidin-4-yl)-2-(1-(3-chlorophenyl)-2-hydroxyethyl)-3,4-dihydropyrrolo[1,2-a]pyrazin-1(2H)-one;
a mixture of (R)- and (S)-7-(2-((2-chloro-4-fluorophenyl)amino)-5-methylpyrimidin-4-yl)-2-(1-(3-chlorophenyl)-2-hydroxyethyl)-3,4-dihydropyrrolo[1,2-a]pyrazin-1 (2H)-one;
(R)-7-(2-((2-chloro-4-fluorophenyl)amino)-5-methylpyrimidin-4-yl)-2-(1-(3-chlorophenyl)ethyl)-3,4-dihydropyrrolo[1,2-a]pyrazin-1(2H)-one;
(S)-7-(2-((2-chloro-4-fluorophenyl)amino)-5-methylpyrimidin-4-yl)-2-(1-(3-chlorophenyl)ethyl)-3,4-dihydropyrrolo[1,2-a]pyrazin-1(2H)-one;
a mixture of (R)- and (S)-7-(2-((2-chloro-4-fluorophenyl)amino)-5-methylpyrimidin-4-yl)-2-(1-(3-chlorophenyl)ethyl)-3,4-dihydropyrrolo[1,2-a]pyrazin-1(2H)-one;
(S)-8-(2-((2-chloro-4-fluorophenyl)amino)-5-methylpyrimidin-4-yl)-2-(1-(3-chlorophenyl)-2-hydroxyethyl)-2,3,4,5-tetrahydro-1H-pyrrolo[1,2-a][1,4]diazepin-1-one;
(R)-8-(2-((2-chloro-4-fluorophenyl)amino)-5-methylpyrimidin-4-yl)-2-(1-(3-chlorophenyl)-2-hydroxyethyl)-2,3,4,5-tetrahydro-1H-pyrrolo[1,2-a][1,4]diazepin-1-one;
a mixture of (R)- and (S)-8-(2-((2-chloro-4-fluorophenyl)amino)-5-methylpyrimidin-4-yl)-2-(1-(3-chlorophenyl)-2-hydroxyethyl)-2,3,4,5-tetrahydro-1H-pyrrolo[1,2-a][1,4]diazepin-1-one;
(S)-7-(2-((2-chloro-4-fluorophenyl)amino)-5-methylpyrimidin-4-yl)-2-(1-(4-chlorophenyl)-2-hydroxyethyl)-3,4-dihydropyrrolo[1,2-a]pyrazin-1(2H)-one;
(R)-7-(2-((2-chloro-4-fluorophenyl)amino)-5-methylpyrimidin-4-yl)-2-(1-(4-chlorophenyl)-2-hydroxyethyl)-3,4-dihydropyrrolo[1,2-a]pyrazin-1(2H)-one;

a mixture of (R)- and (S)-7-(2-((2-chloro-4-fluorophenyl)amino)-5-methylpyrimidin-4-yl)-2-(1-(4-chlorophenyl)-2-hydroxyethyl)-3,4-dihydropyrrolo[1,2-a]pyrazin-1(2H)-one;
(S)-7-(2-((2-chloro-4-fluorophenyl)amino)-5-methylpyrimidin-4-yl)-2-(1-(3-fluorophenyl)-2-hydroxyethyl)-3,4-dihydropyrrolo[1,2-a]pyrazin-1(2H)-one;
(R)-7-(2-((2-chloro-4-fluorophenyl)amino)-5-methylpyrimidin-4-yl)-2-(1-(3-fluorophenyl)-2-hydroxyethyl)-3,4-dihydropyrrolo[1,2-a]pyrazin-1(2H)-one;
A mixture of (R)- and (S)-7-(2-((2-chloro-4-fluorophenyl)amino)-5-methylpyrimidin-4-yl)-2-(1-(3-fluorophenyl)-2-hydroxyethyl)-3,4-dihydropyrrolo[1,2-a]pyrazin-1(2H)-one;
(S)-7-(2-((2-chloro-4-fluorophenyl)amino)-5-methylpyrimidin-4-yl)-2-(1-(4-fluorophenyl)-2-hydroxyethyl)-3,4-dihydropyrrolo[1,2-a]pyrazin-1(2H)-one;
(R)-7-(2-((2-chloro-4-fluorophenyl)amino)-5-methylpyrimidin-4-yl)-2-(1-(4-fluorophenyl)-2-hydroxyethyl)-3,4-dihydropyrrolo[1,2-a]pyrazin-1(2H)-one;
a mixture of (R)- and (S)-7-(2-((2-chloro-4-fluorophenyl)amino)-5-methylpyrimidin-4-yl)-2-(1-(4-fluorophenyl)-2-hydroxyethyl)-3,4-dihydropyrrolo[1,2-a]pyrazin-1(2H)-one;
(S)-7-(2-((2-chloro-4-(piperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(R)-7-(2-((2-chloro-4-(piperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
a mixture of (R)- and (S)-7-(2-((2-chloro-4-(piperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(S)-7-(2-((2-chloro-4-(piperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(R)-7-(2-((2-chloro-4-(piperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1 (2H)-one;
a mixture of (R)- and (S)-7-(2-((2-chloro-4-(piperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(S)-7-(2-((2-chloro-4-(1-isopropylpiperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(R)-7-(2-((2-chloro-4-(1-isopropylpiperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
a mixture of (R)- and (S)-7-(2-((2-chloro-4-(1-isopropylpiperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(S)-7-(2-((2-chloro-4-(1-(methylsulfonyl)piperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(R)-7-(2-((2-chloro-4-(1-(methylsulfonyl)piperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
a mixture of (R)- and (S)-7-(2-((2-chloro-4-(1-(methylsulfonyl)piperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(S)-7-(2-((2-chloro-4-(4-isopropylpiperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(R)-7-(2-((2-chloro-4-(4-isopropylpiperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
a mixture of (R)- and (S)-7-(2-((2-chloro-4-(4-isopropylpiperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(S)-7-(2-((2-chloro-4-(4-(methylsulfonyl)piperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(R)-7-(2-((2-chloro-4-(4-(methylsulfonyl)piperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
a mixture of (R)- and (S)-7-(2-((2-chloro-4-(4-(methylsulfonyl)piperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(S)-2-(1-(3-chlorophenyl)-2-hydroxyethyl)-7-(2-((4-fluorophenyl)amino)-5-methylpyrimidin-4-yl)-3,4-dihydropyrrolo[1,2-a]pyrazin-1(2H)-one;
(R)-2-(1-(3-chlorophenyl)-2-hydroxyethyl)-7-(2-((4-fluorophenyl)amino)-5-methylpyrimidin-4-yl)-3,4-dihydropyrrolo[1,2-a]pyrazin-1(2H)-one;
a mixture of (R)- and (S)-2-(1-(3-chlorphenyl)-2-hydroxyethyl)-7-(2-((4-fluorophenyl)amino)-5-methylpyrimidin-4-yl)-3,4-dihydropyrrolo[1,2-a]pyrazin-1(2H)-one;
(S)-2-(1-(3-chlorophenyl)-2-hydroxyethyl)-7-(5-methyl-2-((tetrahydro-2H-pyran-4-yl)amino)pyrimidin-4-yl)-3,4-dihydropyrrolo[1,2-a]pyrazin-1 (2H)-one;
(R)-2-(1-(3-chlorophenyl)-2-hydroxyethyl)-7-(5-methyl-2-((tetrahydro-2H-pyran-4-yl)amino)pyrimidin-4-yl)-3,4-dihydropyrrolo[1,2-a]pyrazin-1(2H)-one;
a mixture of (R)- and (S)-2-(1-(3-chlorophenyl)-2-hydroxyethyl)-7-(5-methyl-2-((tetrahydro-2H-pyran-4-yl)amino)pyrimidin-4-yl)-3,4-dihydropyrrolo[1,2-a]pyrazin-1(2H)-one;
(R)-2-((4-chloro-3-fluorophenyl)(1-methyl-1H-pyrazol-4-yl)methyl)-7-(5-methyl-2-((tetrahydro-2H-pyran-4-yl)amino)pyrimidin-4-yl)-3,4-dihydropyrrolo[1,2-a]pyrazin-1 (2H)-one;
(S)-2-((4-chloro-3-fluorophenyl)(1-methyl-1H-pyrazol-4-yl)methyl)-7-(5-methyl-2-((tetrahydro-2H-pyran-4-yl)amino)pyrimidin-4-yl)-3,4-dihydropyrrolo[1,2-a]pyrazin-1(2H)-one;
a mixture of (R)- and (S)-2-((4-chloro-3-fluorophenyl)(1-methyl-1H-pyrazol-4-yl)methyl)-7-(5-methyl-2-((tetrahydro-2H-pyran-4-yl)amino)pyrimidin-4-yl)-3,4-dihydropyrrolo[1,2-a]pyrazin-1 (2H)-one;
(S)-2-(1-(3-chlorophenyl)-2-hydroxyethyl)-7-(2-(cyclohexylamino)-5-methylpyrimidin-4-yl)-3,4-dihydropyrrolo[1,2-a]pyrazin-1 (2H)-one;
(R)-2-(1-(3-chlorophenyl)-2-hydroxyethyl)-7-(2-(cyclohexylamino)-5-methylpyrimidin-4-yl)-3,4-dihydropyrrolo[1,2-a]pyrazin-1 (2H)-one;
a mixture of (R)- and (S)-2-(1-(3-chlorophenyl)-2-hydroxyethyl)-7-(2-(cyclohexylamino)-5-methylpyrimidin-4-yl)-3,4-dihydropyrrolo[1,2-a]pyrazin-1(2H)-one;

(S)-2-(1-(3-chlorophenyl)-2-hydroxyethyl)-7-(5-methyl-2-((1-(methylsulfonyl)piperidin-4-yl)amino)pyrimidin-4-yl)-3,4-dihydropyrrolo[1,2-a]pyrazin-1(2H)-one;

(R)-2-(1-(3-chlorophenyl)-2-hydroxyethyl)-7-(5-methyl-2-((1-(methylsulfonyl)piperidin-4-yl)amino)pyrimidin-4-yl)-3,4-dihydropyrrolo[1,2-a]pyrazin-1 (2H)-one; and a mixture of (R)- and (S)-2-(1-(3-chlorophenyl)-2-hydroxyethyl)-7-(5-methyl-2-((1-(methylsulfonyl)piperidin-4-yl)amino)pyrimidin-4-yl)-3,4-dihydropyrrolo[1,2-a]pyrazin-(2H)-one, and/or a pharmaceutically acceptable salt thereof.

Also disclosed herein is a compound selected from the following compounds and/or a pharmaceutically acceptable salt thereof:

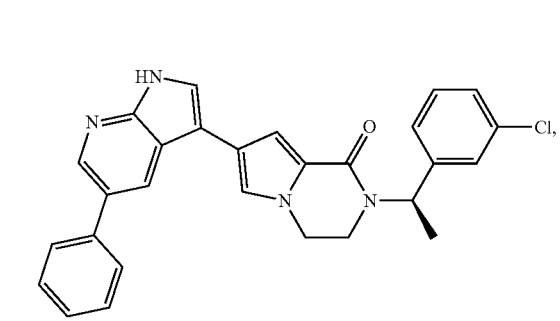

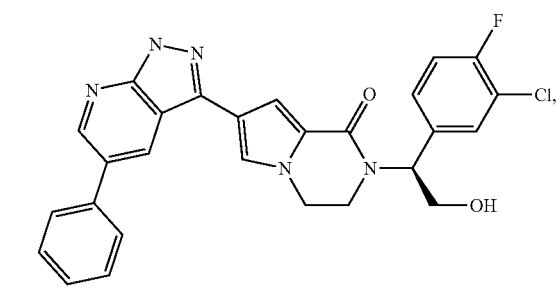

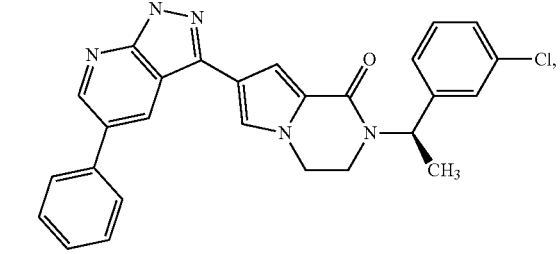

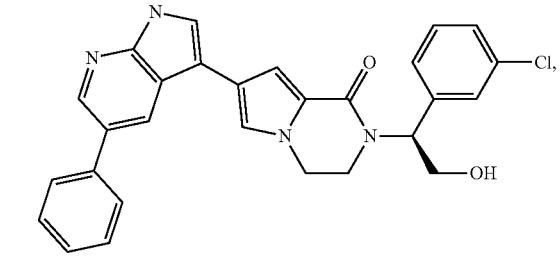

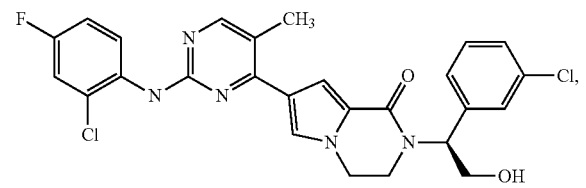

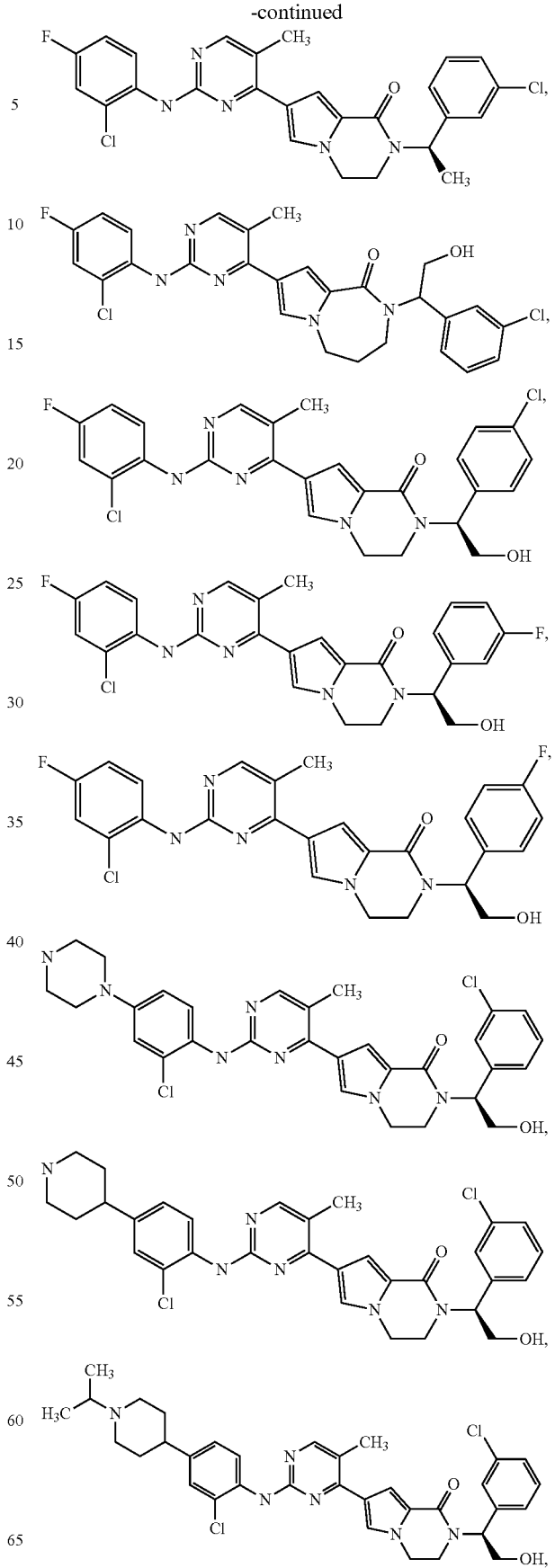

-continued

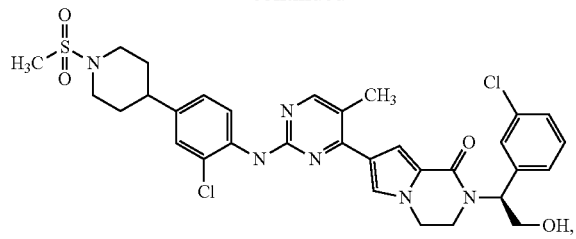
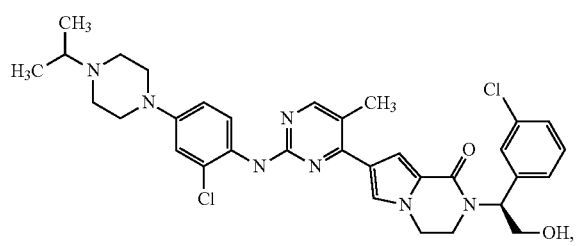
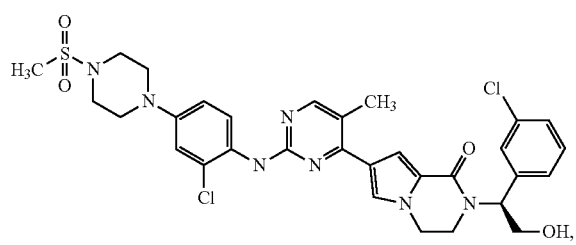
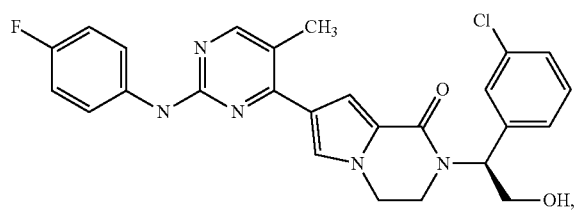
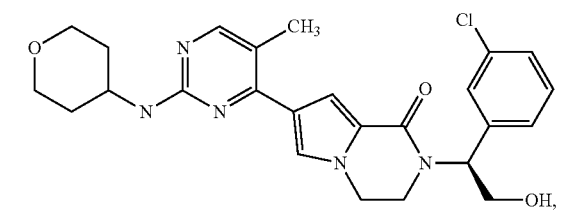
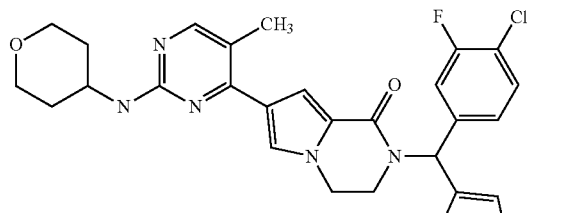
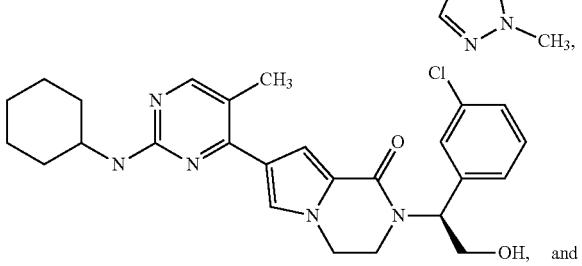

-continued

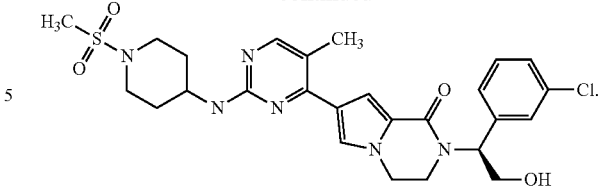

Also disclosed herein is a method of treating a disease treatable by inhibition of Erk in a patient, comprising administering to the patient in recognized need of such treatment, an effective amount of a compound of formula I (such as formulae II and III) and/or a pharmaceutically acceptable salt thereof.

Also disclosed herein is a method of treating a disease treatable by inhibition of Erk in a patient, comprising administering to the patient in recognized need of such treatment, an effective amount of a pharmaceutical composition comprising the compound of formula I (such as formulae II and III) and/or a pharmaceutically acceptable salt thereof, and a pharmaceutically acceptable carrier.

The diseases treatable by inhibition of Erk in a patient include, for example, cancers and inflammatory diseases. Further exemplary diseases include colon cancer, gastric cancer, leukemia, lymphoma, melanoma, pancreate cancer, rheumatoid arthritis, psoriasis, and eczema, Further disclosed herein is a method of treating at least one disease selected from inflammatory diseases and cancers in a patient, comprising administering to the patient in recognized need of such treatment, an effective amount of a pharmaceutical composition comprising a compound of formula I and/or a pharmaceutically acceptable salt thereof disclosed herein and a pharmaceutically acceptable carrier. Exemplary cancers include colon cencer, gastric cancer, leukemia, lymphoma, melanoma, and pancreate cancer. Exemplary inflammatory diseases include rheumatoid arthritis, psoriasis, and eczema.

Also disclosed herein is a pharmaceutical composition comprising a compound of formula I (such as formulae II and III), and/or a pharmaceutically acceptable salt thereof, and a pharmaceutically acceptable carrier.

The pharmaceutical composition comprising a compound of formula I (such as formulae II and III) and/or a pharmaceutically acceptable salt thereof, and a pharmaceutically acceptable carrier, can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The compound of formula I (such as formulae II and III) and/or a pharmaceutically acceptable salt thereof can be administered orally in solid dosage forms, such as capsules, tablets, troches, dragées, granules and powders, or in liquid dosage forms, such as elixirs, syrups, emulsions, dispersions, and suspensions. The compound of formula I (such as formulae II and III) and/or a pharmaceutically acceptable salt thereof can also be administered parenterally, in sterile liquid dosage forms, such as dispersions, suspensions or solutions. Other dosages forms that can also be used to administer the compound of formula I (such as formulae II and III) and/or a pharmaceutically acceptable salt thereof include ointment, cream, drops, transdermal patch or powder for topical administration, an ophthalmic solution or suspension formation, i.e., eye drops, for ocular administration, an aerosol spray or powder composition for inhalation or intranasal administration, or a cream, ointment, spray or suppository for rectal or vaginal administration.

Gelatin capsules containing the compound of formula I (such as formulae II and III) and/or a pharmaceutically acceptable salt thereof and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene gycols can be examples of suitable carriers for parenteral solutions. Solutions for parenteral administration may comprise a water soluble salt of the at least one compound disclosed herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the pharmaceutical composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are disclosed in *Remington's Pharmaceutical Sciences*, A. Osol, a standard reference text in the art.

The compound of formula I (such as formulae II and III) and/or a pharmaceutically acceptable salt thereof can be examined for efficacy in treating cancer by in vivo assays. For example, the compound of formula I (such as formulae II and III) and/or a pharmaceutically acceptable salt thereof can be administered to an animal (e.g., a mouse model) having cancer and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the compound of formula I (such as formulae II and III) and/or a pharmaceutically acceptable salt thereof may be conveniently delivered in the form of an aerosol spray presentation from pressurized packs or nebulisers. The compound of formula I (such as formulae II and III) and/or a pharmaceutically acceptable salt thereof may also be delivered as powders, which may be formulated and the powder composition may be inhaled with the aid of an insufflation powder inhaler device. One exemplary delivery system for inhalation can be a metered dose inhalation (MDI) aerosol, which may be formulated as a suspension or solution of a compound of formula I (such as formulae II and III) and/or a pharmaceutically acceptable salt thereof in at least one suitable propellant, selected, for example, from fluorocarbons and hydrocarbons.

For ocular administration, an ophthalmic preparation may be formulated with an appropriate weight percentage of a solution or suspension of the compound of formula I (such as formulae II and III) and/or a pharmaceutically acceptable salt thereof in an appropriate ophthalmic vehicle, such that the compound of formula I (such as formulae II and III) and/or a pharmaceutically acceptable salt thereof is maintained in contact with the ocular surface for a sufficient time period to allow the compound to penetrate the corneal and internal regions of the eye.

Useful pharmaceutical dosage-forms for administration of the compound of formula I (such as formulae II and III) and/or a pharmaceutically acceptable salt thereof include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, the compound of formula I (such as formulae II and III) and/or a pharmaceutically acceptable salt thereof can be present in an amount of 1, 5, 10, 15, 20, 25, 50, 75, 80, 85, 90, 95, 100, 125, 150, 200, 250, 300, 400 and 500 mg in a capsule.

In some embodiments, a large number of unit capsules can be prepared by filling standard two-piece hard gelatin capsules each with, for example, 100 milligrams of the compound of formula I (such as formulae II and III) and/or a pharmaceutically acceptable salt thereof in powder, 150 milligrams of lactose, 50 milligrams of cellulose, and 6 milligrams magnesium stearate.

In some embodiments, a mixture of the compound of formula I (such as formulae II and III) and/or a pharmaceutically acceptable salt thereof and a digestible oil such as soybean oil, cottonseed oil or olive oil can be prepared and injected by means of a positive displacement pump into gelatin to form soft gelatin capsules containing 75 or 100 milligrams of the active ingredient. The capsules are washed and dried.

In some embodiments, the compound of formula I (such as formulae II and III) and/or a pharmaceutically acceptable salt thereof can be present in an amount of 1, 5,10, 15, 20, 25, 50, 75, 80, 85, 90, 95, 100, 125, 150, 200, 250, 300, 400 and 500 mg in a tablet.

In some embodiments, a large number of tablets can be prepared by conventional procedures so that the dosage unit comprises, for example, 100 milligrams of the compound of formula I (such as formulae II and III) and/or a pharmaceutically acceptable salt thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may, for example, be applied to increase palatability or delay absorption.

In some embodiments, a parenteral composition suitable for administration by injection can be prepared by stirring 1.5% by weight of the a compound of formula I (such as formulae II and III) and/or a pharmaceutically acceptable salt thereof in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound of formula I (such as formulae II and III) and/or a pharmaceutically acceptable salt thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound of formula I (such as formulae II and III) and/or a pharmaceutically acceptable salt thereof are administered stepwise or in conjunction with at least one other therapeutic agent. When drugs are administered in physical combination, the dosage form and administration route should be selected depending on the compatibility of the combined drugs. Thus, the term "co-administration" is understood to include the administration of at least two agents concomitantly or sequentially, or alternatively as a fixed dose combination of the at least two active components.

The compound of formula I (such as formulae II and III) and/or a pharmaceutically acceptable salt thereof can be administered as the sole active ingredient or in combination with at least one second active ingredient, selected, for example, from other active ingredients known to be useful for treating the target disease, such as cancers including, for example, colon cancer, gastric cancer, leukemia, lymphoma, melanoma, and pancreate cancer in a patient.

Synthesis of Compounds

Set forth below are some non-limiting exemplary synthetic schemes that have been used or can be used for synthesizing the compound of formula I:

Scheme A:

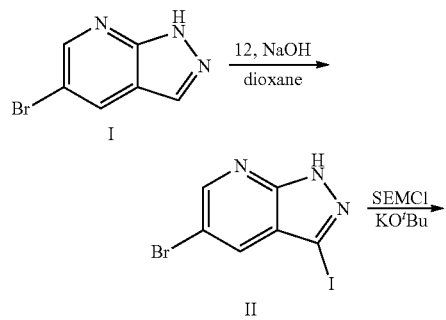

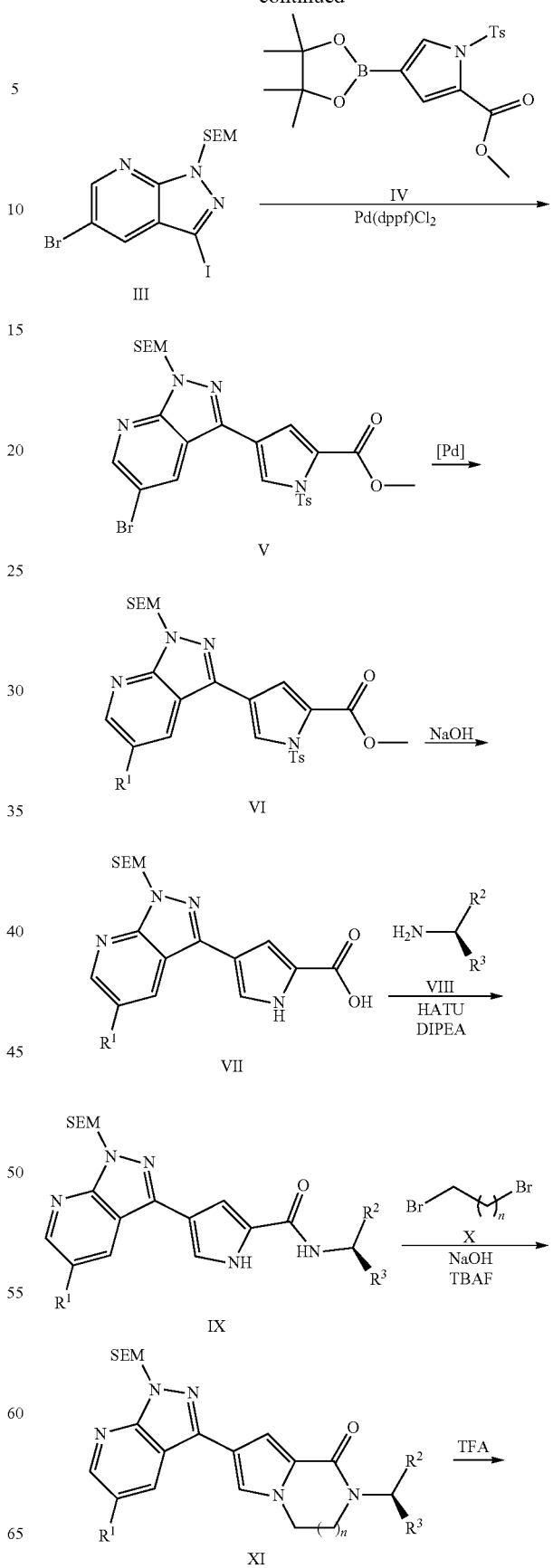

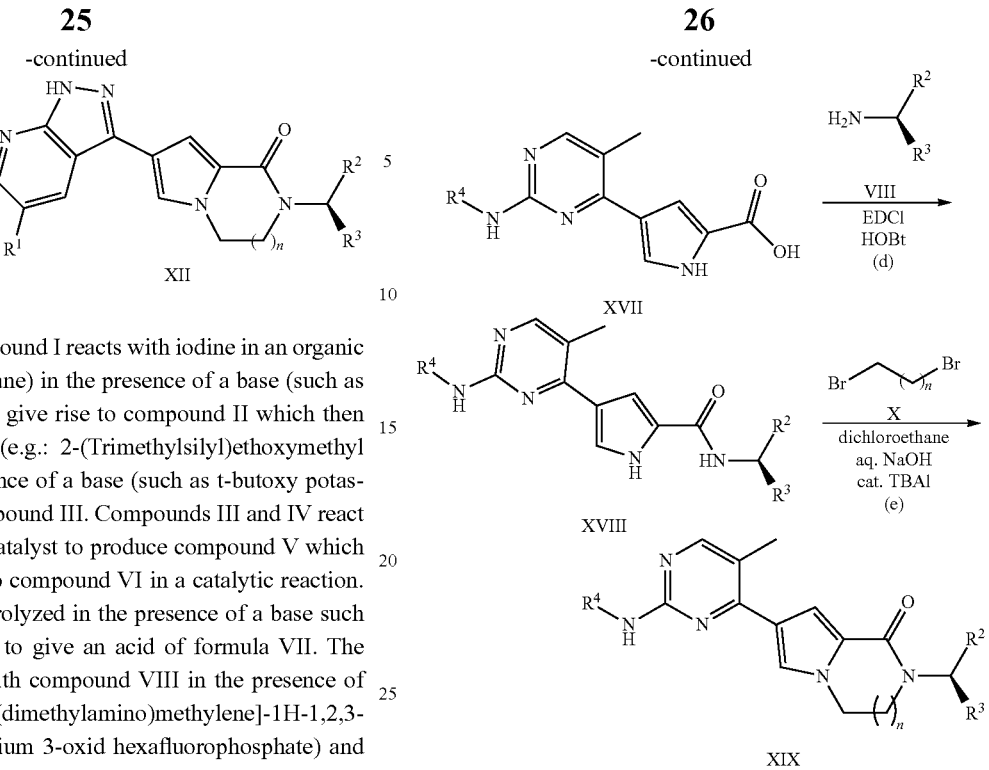

In Scheme A, compound I reacts with iodine in an organic solvent (such as dioxane) in the presence of a base (such as sodium hydroxide) to give rise to compound II which then reacts with SEM-Cl (e.g.: 2-(Trimethylsilyl)ethoxymethyl chloride) in the presence of a base (such as t-butoxy potassium) to provide compound III. Compounds III and IV react in the presence of a catalyst to produce compound V which in turn is converted to compound VI in a catalytic reaction. Compound VI is hydrolyzed in the presence of a base such as sodium hydroxide to give an acid of formula VII. The product is coupled with compound VIII in the presence of HATU (e.g., 1-[Bis(dimethylamino)methylene]-1H-1,2,3-triazolo[4,5-b]pyridinium 3-oxid hexafluorophosphate) and amine to give rise to compound IX. Compound IX and X react in the presence of a base (such as sodium hydroxide) to produce the cyclized compound XI, which finally is reduced, e.g., in the presence of TFA (trifuloroacetic acid), to give compound X.

Scheme B:

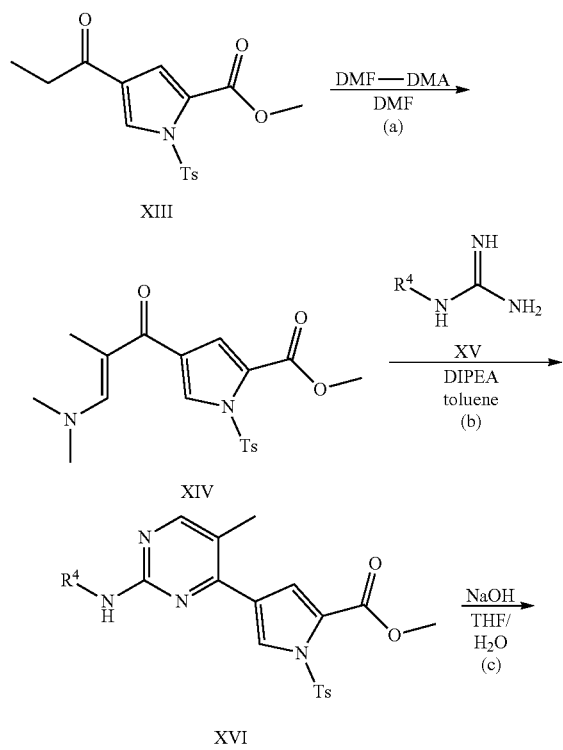

Scheme B above shows another general synthetic route that can be used for preparing compounds of formula I. In step (a), compound XIII is combined with DMF-DMA in DMF at 70° C. to form compound XIV. Compound XVI in step (b) is obtained by treating compound XIV with N-substituted guanidine XV in the presence of base (e.g., DIPEA) in toluene. Compound XVI is subsequently hydrolyzed in a basic condition such as sodium hydroxide in THF/water to give acid XVII which is then coupled with amine VIII in the presence of EDCI/HOBt in organic solvent (e.g., NMP) to form compound XVIII. In step (e), compound XVIII is treated with compound X in the presence of base (e.g., sodium hydroxide) to form the cyclized compound XIX.

In the following examples, the abbreviations below are used:
DCM dichloromethane
DHP 3,4-Dihydro-2H-pyran
DIPEA di-isopropylethylamine
DMF dimethylformamide
DMF-DMA N,N-Dimethylformamide dimethyl acetal
EDCI 1-ethyl-3-(-3-dimethyaminopropyl)carbodiimide
EtOAc ethyl acetate
HATU 1-[Bis(dimethylamino)methylene]-1H-1,2,3-triazolo[4,5-b]pyridinium 3-oxid hexafluorophosphate
HOBt 1-Hydroxy-1H-benzontriazole
MeOH methanol
NMP N-methyl-2-pyrrolidone
Pd(dppf)Cl2 [1,1'-Bis(diphenylphosphino)ferrocene]dichloropalladium(II)
PE Petroleum ether
PPTS Pyridinium p-toluenesulfonate
SEMCl 2-(Trimethylsilyl)ethoxymethyl chloride
TBAF Tetrabutylammonium fluoride
TBAI Tetrabutylammonium iodide
t-BuOK Potassium tert-butoxide
TLC Thin layer chromatograhpy
TFA trifluoacetic acid
THF tetrahydrofuran

EXAMPLE 1: SYNTHESIS OF (R)-2(1-(3-CHLOROPHENYL)ETHYL)-7-(5-PHENYL-1-((2-(TRIMETHYLSILYL)ETHOXY)METHYL)-1H-PYRAZOLO[3,4-B]PYRIDIN-3-YL)-3,4-DIHYDROPYRROLO[1,2-A]PYRAZIN-1(2H)-ONE

The title compound was synthesized according to Scheme A as set forth below.

Step 1 Preparation of 5-bromo-3-iodo-1H-pyrazolo[3,4-b]pyridine (II)

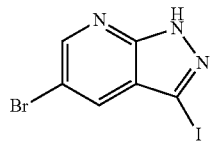 [SMILES: Brc1cnc2[nH]nc(I)c2c1]

To a solution of 5-bromo-1H-pyrazolo[3,4-b]pyridine (I) (5 g, 25.25 mmol, 1 eq) in a mixture of 1,4-dioxane (100 mL) and 4 N aqueous NaOH (100 mL) was added iodine (64.1 g, 252.5 mmol, 10 eq). The resulting mixture was stirred at 60° C. overnight, and TLC showed the reaction was complete. The resulting mixture was extracted with EtOAc (100 ml×2). The combined organic layers were washed with saturated aqueous NaHSO₃ (100 mL×3) and brine (50 mL), dried over Na₂SO₄, and concentrated to give the title compound 5-bromo-3-iodo-1H-pyrazolo[3,4-b]pyridine (11) as an off-white solid (7.5 g, yield: 91%), which was used in the next step without any further purification.

Step 2 Preparation of 5-bromo-3-iodo-1-((2-(trimethylsilyl)ethoxy)methyl)-1H-pyrazolo[3,4-b]pyridine (III)

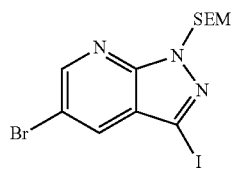 [SMILES: C[Si](C)(C)CCOCn1nc(I)c2cc(Br)cnc21]

To a solution of 5-bromo-3-iodo-1H-pyrazolo[3,4-b]pyridine (II) (7.5 g, 23.15 mmol, 1 eq) and t-BuOK (3.12 g, 27.78 mmol, 1.2 eq) in DMF (75 mL) was added SEMCl (4.63 g, 27.78 mmol, 1.2 eq) dropwise at 0° C. The mixture was allowed to warm to r.t. and stirred overnight. TLC showed the reaction was complete. The reaction mixture was extracted with EtOAc (100 ml×2). The combined organic layers were washed with Na₂CO₃ (100 ml×2) and brine (50 ml), dried over anhydrous Na₂SO₄, and concentrated. The residue was purified by silica gel column chromatography (petroleum ether:EtOAc=20:1) to give the title compound 5-bromo-3-iodo-1-((2-(trimethylsilyl)ethoxy)methyl)-1H-pyrazolo[3,4-b]pyridine (III) as off-white solid (7.5 g, yield: 71.3%).

Step 3 Preparation of Methyl 4-(5-bromo-1-((2-(trimethylsilyl)ethoxy)methyl)-1H-pyrazolo[3,4-b]pyridin-3-yl)-1-tosyl-1H-pyrrole-2-carboxylate (V)

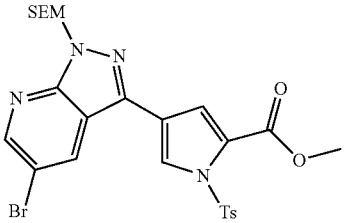 [SMILES: COC(=O)c1cc(-c2nn(COCC[Si](C)(C)C)c3ncc(Br)cc23)cn1S(=O)(=O)c1ccc(C)cc1]

A solution of 5-bromo-3-iodo-1-((2-(trimethylsilyl)ethoxy)methyl)-1H-pyrazolo[3,4-b] pyridine (III) (5 g, 11 mmol, 1 eq), methyl 4-(4,4,5,5-tetramethyl-1,3,2-dioxaborolan-2-yl)-1-tosyl-1H-pyrrole-2-carboxylate (IV) (5.27 g, 13 mmol, 1.2 eq), Pd(dppf)Cl₂ (402 mg, 0.55 mmol, 0.05 eq.), and Na₂CO₃ (2.322 g, 22 mmol, 2 eq.) in DMF (50 mL) and H₂O (5 mL) was stirred at 50° C. for approximately 140 minutes. The reaction mixture was filtered, and the filtrate was extracted with EtOAc (100 mL×3). The combined organic layers were washed with H₂O (100 ml×3) and brine (50 ml×2), dried over anhydrous Na₂SO₄, and concentrated. The residue was purified by silica gel column chromatography (Petroleum ether:EtOAc=20:1~15:1) to give the title compound methyl 4-(5-bromo-1-((2-(trimethylsilyl)ethoxy)methyl)-1H-pyrazolo[3,4-b]pyridin-3-yl)-1-tosyl-1H-pyrrole-2-carboxylate (V) as off-white solid (3.17 g, yield: 47.6%).

Step 4 Preparation of Methyl 4-(5-phenyl-1-((2-(trimethylsilyl)ethoxy)methyl)-1H-pyrazolo[3,4-b]pyridine-3-yl)-1-tosyl-1H-pyrrole-2-carboxylate (VI)

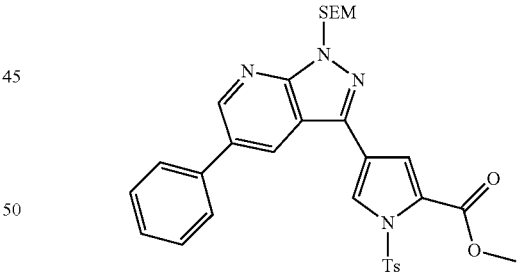

A solution of methyl 4-(5-bromo-1-((2-(trimethylsilyl)ethoxy)methyl)-1H-pyrazolo[3,4-b]pyridin-3-yl)-1-tosyl-1H-pyrrole-2-carboxylate (V) (580 mg, 0.96 mmol, 1.0 eq), phenylboronic acid (130 mg, 0.528 mmol, 1.1 eq.), Na₂CO₃ (204 mg, 0.960 mmol, 2.0 eq.), and Pd(dppf)Cl₂ (70 mg, 0.048 mmol, 0.1 eq.) in DMF (10 mL) and H₂O (2 mL) was stirred under nitrogen at 65° C. for approximately 100 minutes. The mixture was filtered. The filtrate was diluted with EtOAc (50 mL) and water (20 mL). The organic layer was separated, washed with brine (20 mL×3), dried over Na₂SO₄, and concentrated. The residue was purified by silica gel column chromatography (PE:EtOAc=3:1) to give the title compound methyl 4-(5-phenyl-1-((2-(trimethylsilyl)ethoxy)methyl)-1H-pyrazolo[3,4-b]pyridin-3-yl)-1-to-syl-1H-pyrrole-2-carboxylate (VI) (281 mg, yield: 48%).

Step 5 Preparation of 4-(5-phenyl-1-((2-(trimethyl-silyl)ethoxy)methyl)-1H-pyrazolo[3,4-b]pyridin-3-yl)-1H-pyrrole-2-carboxylic acid (VII)

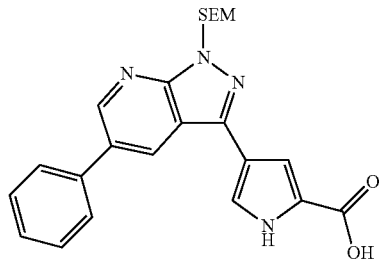 [SMILES: C[Si](C)(C)CCOCn1nc(-c2c[nH]c(C(=O)O)c2)c2cc(-c3ccccc3)cnc21]

A solution of 4-(5-phenyl-1-((2-(trimethylsilyl)ethoxy) methyl)-1H-pyrazolo[3,4-b]pyridin-3-yl)-1-tosyl-1H-pyrrole-2-carboxylate (VI) (1.58 g, 2.63 mmol, 1.0 eq.) and NaOH (0.53 mg, 13.1 mmol, 5.0 eq.) in THF (8 mL) and $H_2O$ (8 mL) was stirred at 90° C. for approximately 18 hours. TLC showed the reaction was complete. The reaction mixture was cooled to r.t. and concentrated to remove majority of MeOH. The resultant aqueous solution was acidified to PH=~3 with concentrated hydrochloric acid and extracted with EtOAc (50 mL). The organic layer was washed with $H_2O$ (20 mL) and brine (20 mL), dried over $Na_2SO_4$, and concentrated. The residue was purified by silica gel column chromatography (MeOH:DCM=10:1) to give the title compound 4-(5-phenyl-1-((2-(trimethylsilyl) ethoxy)methyl)-H-pyrazolo[3,4-b]pyridin-3-yl)-1H-pyrrole-2-carboxylic acid (VII) (1.0 g, yield: 87%).

Step 6 (R)—N-(1-(3-chlorophenyl)ethyl)-4-(5-phe-nyl-1-((2-(trimethylsilyl)ethoxy)methyl)-1H-pyra-zolo[3,4-b]pyridin-3-yl)-1H-pyrrole-2-carboxamide (IX)

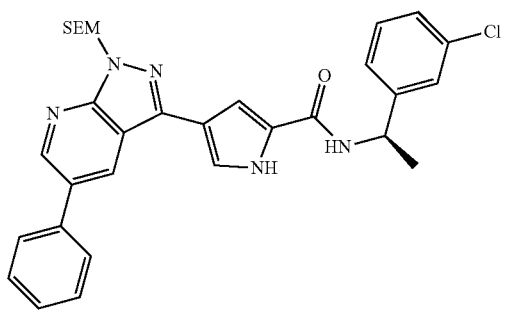 [SMILES: C[C@@H](NC(=O)c1cc(-c2nn(COCC[Si](C)(C)C)c3ncc(-c4ccccc4)cc23)c[nH]1)c1cccc(Cl)c1]

To a solution of 4-(5-phenyl-1-((2-(trimethylsilyl)ethoxy) methyl)-1H-pyrazolo[3,4-b]pyridin-3-yl)-1H-pyrrole-2-carboxylic acid (VII) (100 mg, 0.23 mmol), HATU (106 mg, 0.28 mmol) in DCM (1.5 mL) was added DIPEA (59 mg, 0.46 mmol). The mixture was stirred at r.t. overnight. The mixture was concentrated, and partitioned between EtOAc (50 mL) and $H_2O$ (20 mL). The organic layer was collected, washed with brine (20 mL), dried over $Na_2SO_4$, and concentrated to give the title compound (R)—N-(1-(3-chloro-phenyl)ethyl)-4-(5-phenyl-1-((2-(trimethylsilyl)ethoxy) methyl)-1H-pyrazolo[3,4-b]pyridin-3-yl)-1H-pyrrole-2-carboxamide (IX) (90 mg, yield: 68%).

Step 7 (R)-2-(1-(3-chlorophenyl)ethyl)-7-(5-phenyl-1-((2-(trimethylsilyl)ethoxy)methyl)-1H-pyrazolo[3,4-b]pyridin-3-yl)-3,4-dihydropyrrolo[1,2-a]pyrazin-1(2H)-one (XI)

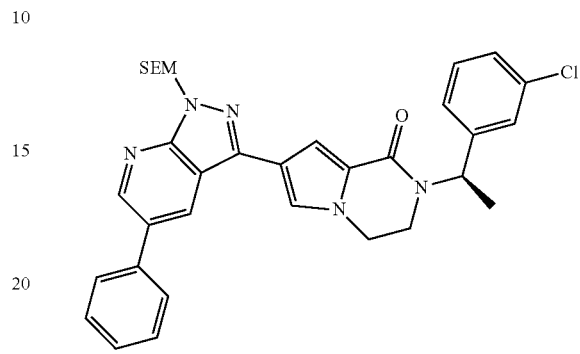

To a solution of (R)—N-(1-(3-chlorophenyl)ethyl)-4-(5-phenyl-1-((2-(trimethylsilyl)ethoxy)methyl)-1H-pyrrolo[2,3-b]pyridin-3-yl)-1H-pyrrole-2-carboxamide (IX) (150 mg, 0.263 mmol) and 1,2-dibromoethane (X) (489 mg, 2.63 mmol) in 1,2-dichloroethane (3 mL) was added 1M NaOH (2.63 mL) and 1M TBAF/THF (0.3 mL). The mixture was stirred at 100° C. for approximately 12 hours, extracted with EtOAc (50 mL), and washed with brine (20 mL×2). The organic layer dried over anhydrous $Na_2SO_4$, filtered, and concentrated. The residue was purified by column chromatography (Petrolium Ether:EtOAc=5:1) to give the title compound (R)-2-(1-(3-chlorophenyl)ethyl)-7-(5-phenyl-1-((2-(trimethylsilyl)ethoxy)methyl)-1H-pyrrolo[2,3-b]pyridin-3-yl)-3,4-dihydropyrrolo[1,2-a]pyrazin-(2H)-one (XI) (54 mg, yield: 34%).

Step 8 (R)-2-(1-(3-chlorophenyl)ethyl)-7-(5-phenyl-1H-pyrrolo[2,3-b]pyridin-3-yl)-3,4-dihydropyrrolo [1,2-a]pyrazin-1 (2H)-one (XII)

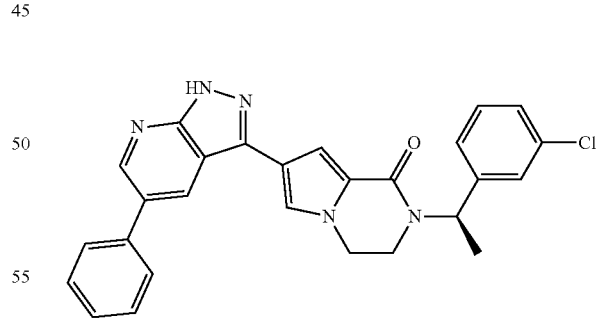

A solution of (R)-2-(1-(3-chlorophenyl)ethyl)-7-(5-phe-nyl-1-((2-(trimethylsilyl)ethoxy)methyl)-1H-pyrrolo[2,3-b] pyridin-3-yl)-3,4-dihydropyrrolo[1,2-a]pyrazin-1(2H)-one (XI) (54 mg, 0.09 mmol) in DCM/TFA (4 mL/2 mL) was stirred at 30° C. for approximately 2 hours. The mixture was concentrated. The residue was suspended in MeOH/ammo-nia (2 mL/2 mL), and stirred at 30° C. overnight. The mixture was extracted with EtOAc (50 mL). The EtOAc layer was washed with brine (20 mL), dried over anhydrous Na$_2$SO$_4$, and concentrated. The residue was purified by prep-TLC to give the title compound (R)-2-(1-(3-chlorophenyl)ethyl)-7-(5-phenyl-1H-pyrrolo[2,3-b]pyridin-3-yl)-3,4-dihydropyrrolo[1,2-a]pyrazin-1(2H)-one (XII) (24 mg, yield: 58%).

Table 1 lists the compound of Example 1 and compounds that were prepared according to the procedures of Example 1 by using the corresponding intermediates and reagents under appropriate conditions that could be recognized by one skilled in the art.

TABLE 1

| Compound No. | STRUCTURE | Chemical Name | LCMS (M + H) | 1H NMR (400 MHz) |
|---|---|---|---|---|
| 1 | 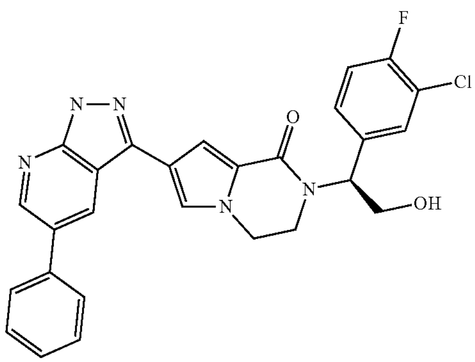 [SMILES: O=C1c2cc(-c3n[nH]c4ncc(-c5ccccc5)cc34)cn2CCN1[C@H](CO)c1ccc(F)c(Cl)c1] | (S)-2-(1-(3-chloro-4-fluorophenyl)-2-hydroxyethyl)-7-(5-phenyl-1H-pyrazolo[3,4-b]pyridin-3-yl)-3,4-dihydropyrrolo[1,2-a]pyrazin-1(2H)-one | 502.1 | $^1$H-NMR (400 MHz, CD$_3$OD: δ 8.79 (1H, s), δ 8.58 (1H, s), 7.73 (2H, d, J = 8.0 Hz), 7.62-7.49 (m, 5H), 7.41-7.37 (m, 2H), 7.25 (1H, d, J = 7.2 Hz), 5.87 (1H, t), 4.19-4.08 (m, 3H), 3.84 (1H, t), 3.51 (2H, t). |
| 2 | 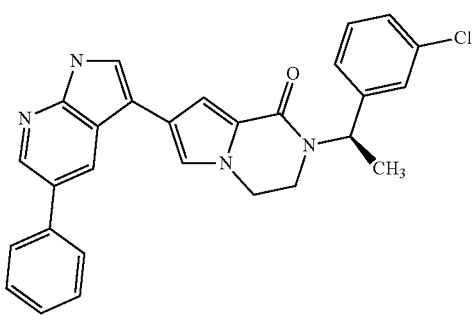 [SMILES: C[C@H](c1cccc(Cl)c1)N1CCn2cc(-c3c[nH]c4ncc(-c5ccccc5)cc34)cc2C1=O] | (R)-2-(1-(3-chlorophenyl)ethyl)-7-(5-phenyl-1H-pyrrolo[2,3-b]pyridin-3-yl)-3,4-dihydropyrrolo[1,2-a]pyrazin-1(2H)-one | 467.2 | $^1$H NMR (400 MHz, CDCl3) δ 10.55 (s, 1H), 8.60 (s, 1H), 8.32 (s, 1H), 7.67 (d, J = 7.5 Hz, 2H), 7.50 (t, J = 7.3 Hz, 3H), 7.43-7.35 (m, 2H), 7.30 (d, J = 4.9 Hz, 3H), 7.02 (s, 1H), 6.20 (q, J = 6.9 Hz, 1H), 4.07 (ddd, J = 16.7, 12.3, 7.7 Hz, 2H), 3.68-3.53 (m, 1H), 3.34-3.16 (m, 1H), 1.60 (d, J = 7.0 Hz, 3H). |
| 3 | 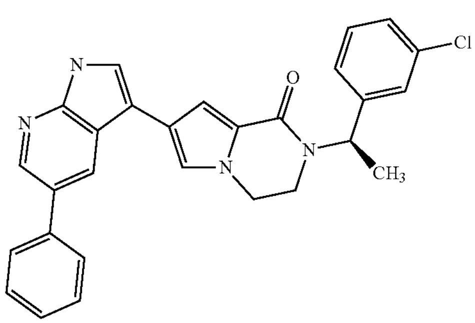 [SMILES: C[C@H](c1cccc(Cl)c1)N1CCn2cc(-c3c[nH]c4ncc(-c5ccccc5)cc34)cc2C1=O] | (R)-2-(1-(3-chlorophenyl)ethyl)-7-(5-phenyl-1H-pyrazolo[3,4-b]pyridin-3-yl)-3,4-dihydropyrrolo[1,2-a]pyrazin-1(2H)-one | 468.2 | $^1$H-NMR (400 MHz, CD$_3$OD): δ 8.69 (1H, s), δ 8.46 (1H, s), 7.66 (2H, d, J = 7.6 Hz), 7.50-7.27 (m, 9H), 6.01 (1H, t), 4.17-4.15 (m, 1H), 4.08-4.05 (m, 1H), 3.67-3.64 (m, 1H), 3.29-3.24 (m, 1H), 1.59 (3H, s). |
| 4 | 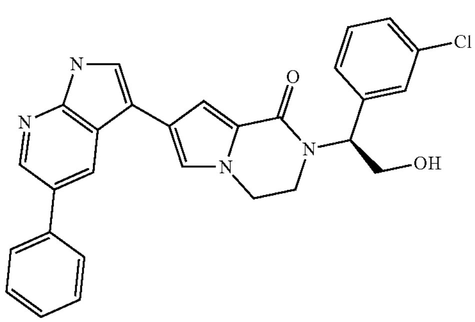 [SMILES: O=C1c2cc(-c3c[nH]c4ncc(-c5ccccc5)cc34)cn2CCN1[C@H](CO)c1cccc(Cl)c1] | (S)-2-(1-(3-chlorophenyl)-2-hydroxyethyl)-7-(5-phenyl-1H-pyrrolo[2,3-b]pyridin-3-yl)-3,4-dihydropyrrolo[1,2-a]pyrazin-1(2H)-one | 483.2 | $^1$H NMR (400 MHz, CD$_3$OD) δ 8.44 (s, 1H), 8.39 (d, J = 2.0 Hz, 1H), 7.69 (d, J = 7.9 Hz, 3H), 7.56 (s, 1H), 7.47 (t, J = 7.6 Hz, 3H), 7.42-7.32 (m, 3H), 7.30 (s, 1H), 7.20 (d, J = 1.6 Hz, 1H), 5.99 (t, J = 6.6 Hz, 1H), 4.14 (t, J = 6.4 Hz, 4H), 3.81-3.67 (m, 1H), 3.46-3.35 (m, 1H). |

EXAMPLE 2: SYNTHESIS OF (S)-2-(1-(3-CHLOROPHENYL)-2-HYDROXYETHYL)-7-(5-METHYL-2-((TETRAHYDRO-2H-PYRAN-4-YL)AMINO)PYRIMIDIN-4-YL)-3,4-DIHYDROPYRROLO-[1,2-A]PYRAZIN-1(2H)-ONE

The title compound was synthesized according to Scheme B as set for below.

Step 1 Preparation of methyl 4-(3-(dimethylamino)-2-methylacryloyl)-1-tosyl-1H-pyrrole-2-carboxylate

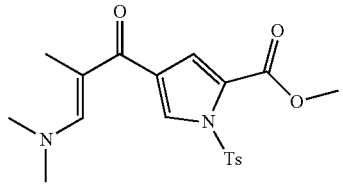

To a solution of methyl 4-propionyl-1-tosyl-1H-pyrrole-2-carboxylate (30 g, 89.5 mmol) in DMF (200 mL) was added DMF-DMA (53 g, 895 mmol). The mixture was stirred at 70° C. for approximately 18 hours and concentrated under reduced pressure to remove majority of DMF. The residue was taken in EtOAc (400 mL), which was then washed with brine (100 mL×3), dried over $Na_2SO_4$, and concentrated to give the crude methyl 4-(3-(dimethylamino)-2-methylacryloyl)-1-tosyl-1H-pyrrole-2-carboxylate (30 g, crude yield: 80%), which was used in the next step without any further purification.

Step 2 methyl 4-(5-methyl-2-((tetrahydro-2H-pyran-4-yl)amino)pyrimidin-4-yl)-1-tosyl-1H-pyrrole-2-carboxylate

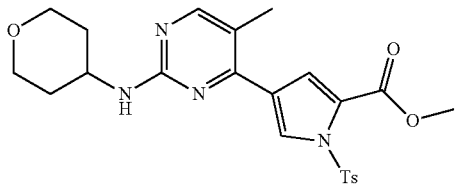 [SMILES: COC(=O)c1cc(-c2nc(NC3CCOCC3)ncc2C)cn1S(=O)(=O)c1ccc(C)cc1]

To a solution of methyl 4-(3-(dimethylamino)-2-methylacryloyl)-1-tosyl-1H-pyrrole-2-carboxylate (30 g, 77 mol) and 1-(tetrahydro-2H-pyran-4-yl)guanidine hydrochloride (19.6 g, 109 mmol) in toluene (300 mL) was added DIPEA (10 g, 77 mmol). The mixture was heated to reflux for 20 h using a Dean-Stark trap to collect water. The mixture was cooled slightly and concentrated to remove the solvent. The residue was triturated with methanol (100 mL), and the resulting solid was collected by filtration to give the title compound methyl 4-(5-methyl-2-((tetrahydro-2H-pyran-4-yl)amino)pyrimidin-4-yl)-1-tosyl-1H-pyrrole-2-carboxylate (18 g, yield: 50%).

Step 3 4-(5-methyl-2-((tetrahydro-2H-pyran-4-yl)amino)pyrimidin-4-yl)-1H-pyrrole-2-carboxylic acid

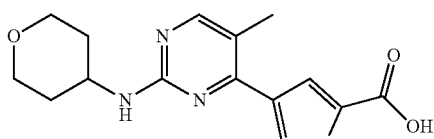

To a solution of methyl 4-(methyl-2-((tetrahydro-2H-pyran-4-yl)amino)pyrimidin-4-yl)-1-tosyl-1H-pyrrole-2-carboxylate (8.0 g, 17 mmol) in THF (80 mL) was added 1N NaOH (85 mL, 85 mmol). The mixture was heated to reflux for approximately 18 hours, cooled to r.t, adjusted to PH=4 using 6N hydrochloric acid (~15 mL), and concentrated under reduced pressure to remove majority of THF. The resulting suspension was filtered. The filter cake was dried under vacuum to give the title compound 4-(5-methyl-2-((tetrahydro-2H-pyran-4-yl)amino)pyrimidin-4-yl)-1H-pyrrole-2-carboxylic acid (4.6 g, yield: 90%).

Step 4 (S)—N-(1-(3-chlorophenyl)-2-hydroxyethyl)-4-(5-methyl-2-((tetrahydro-2H-pyran-4-yl)amino)pyrimidin-4-yl)-1H-pyrrole-2-carboxamide

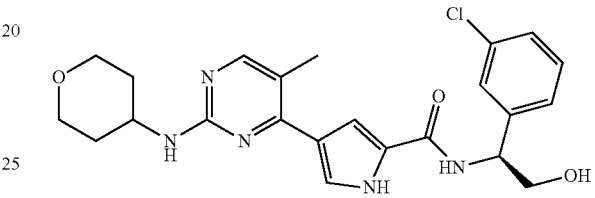

To a solution of 4-(5-methyl-2-((tetrahydro-2H-pyran-4-yl)amino)pyrimidin-4-yl)-1H-pyrrole-2-carboxylic acid (2.5 g, 8.3 mmol), (S)-2-amino-2-(3-chlorophenyl)ethanol (1.7 g, 10 mmol), HOBt (1.35 g, 10 mmol), EDCI (3.2 g, 16.6 mmol) in NMP (30 mL) was added DIPEA (2.1 g, 16.6 mmol). The mixture was stirred at r.t for 20 h, diluted with water (50 mL), and extracted with EtOAc (200 mL). The organic layer was washed with water (50 mL×3) and brine (50 mL), dried over $Na_2SO_4$ and concentrated. The residue was purified by column chromatography (DCM:MeOH=100:1 to 40:1) to give the title compound (S)—N-(1-(3-chlorophenyl)-2-hydroxyethyl)-4-(5-methyl-2-((tetrahydro-2H-pyran-4-yl)amino)pyrimidin-4-yl)-1H-pyrrole-2-carboxamide (3.1 g, yield: 80%).

Step 5 N-((1S)-1-(3-chlorophenyl)-2-((tetrahydro-2H-pyran-2-yl)oxy)ethyl)-4-(5-methyl-2-((tetrahydro-2H-pyran-4-yl)amino)pyrimidin-4-yl)-1H-pyrrole-2-carboxamide

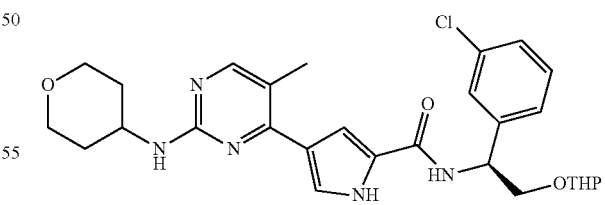

To a solution of (S)—N-(1-(3-chlorophenyl)-2-hydroxyethyl)-4-(5-methyl-2-((tetrahydro-2H-pyran-4-yl)amino)pyrimidin-4-yl)-1H-pyrrole-2-carboxamide (4.6 g, 10.1 mmol) and PPTS (1.0 g, 4 mmol) in THF (50 mL) was adde DHP (2.1 g, 25.3 mmol). The mixture was heated to reflux for approximately 18 hours, cooled to r.t., diluted with water (100 mL), and extracted with EtOAc (200 mL). The organic layer was washed with brine (100 mL), dried over $Na_2SO_4$ and concentrated. The residue was purified by silica gel column chromatography to give the title compound N-((1 S)-1-(3-chlorophenyl)-2-((tetrahydro-2H-pyran-2-yl)oxy)ethyl)-4-(5-methyl-2-((tetrahydro-2H-pyran-4-yl)amino)pyrimidin-4-yl)-1H-pyrrole-2-carboxamide (3.2 g, yield: 60%).

Step 6 2-((1S)-1-(3-chlorophenyl)-2-((tetrahydro-2H-pyran-2-yl)oxy)ethyl)-7-(5-methyl-2-((tetrahydro-2H-pyran-4-yl)amino)pyrimidin-4-yl)-3,4-dihydropyrrolo[1,2-a]pyrazin-1(2H)-one

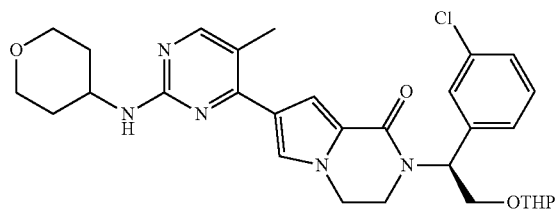

To a solution of N-((1 S)-1-(3-chlorophenyl)-2-((tetrahydro-2H-pyran-2-yl)oxy)ethyl)-4-(5-methyl-2-((tetrahydro-2H-pyran-4-yl)amino)pyrimidin-4-yl)-1H-pyrrole-2-carboxamide (3.0 g, 5.56 mmol) in 1,2-dichloroethane (30 mL) was added 1,2-dibromoethane (10.5 g, 55.6 mmol), TBAI (410 mg, 1.1 mmol), and 1N NaOH (55.6 mL, 55.6 mmol). The mixture was stirred at 80° C. for approximately 2 hours, cooled to r.t., and diluted with DCM (50 mL). The organic layer was washed with brine (20 mL×3), dried over Na$_2$SO$_4$, and concentrated. The residue was purified by column chromatography (DCM:MeOH=100:1 to 40:1) to give the title compound 2-((1S)-1-(3-chlorophenyl)-2-((tetrahydro-2H-pyran-2-yl)oxy)ethyl)-7-(5-methyl-2-((tetrahydro-2H-pyran-4-yl)amino)pyrimidin-4-yl)-3,4-dihydropyrrolo[1,2-a]pyrazin-1 (2H)-one (2.6 g, yield: 82%).

Step 7 (S)-2-(1-(3-chlorophenyl)-2-hydroxyethyl)-7-(5-methyl-2-((tetrahydro-2H-pyran-4-yl)amino)pyrimidin-4-yl)-3,4-dihydropyrrolo[1,2-a]pyrazin-1(2H)-one

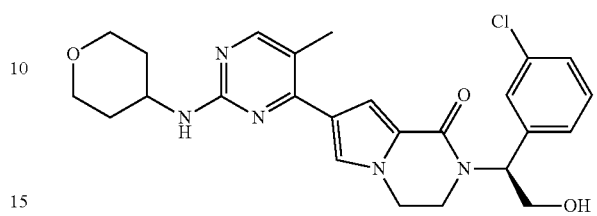

To a solution of 2-((1 S)-1-(3-chlorophenyl)-2-((tetrahydro-2H-pyran-2-yl)oxy)ethyl)-7-(5-methyl-2-((tetrahydro-2H-pyran-4-yl)amino)pyrimidin-4-yl)-3,4-dihydropyrrolo[1,2-a]pyrazin-1(2H)-one (2.4 g, 4.24 mmol) in MeOH (24 mL) was added PPTS (430 mg, 1.7 mmol). The mixture was heated to reflux for approximately 18 hours, cooled to r.t., and concentrated. The residue was taken up in EtOAc (100 mL), which was washed with brine (50 mL), dried over Na$_2$SO$_4$, and concentrated. The residue was purified by column chromatography (DCM:MeOH=100:1 to 20:1) to give the title compound (S)-2-(1-(3-chlorophenyl)-2-hydroxyethyl)-7-(5-methyl-2-((tetrahydro-2H-pyran-4-yl)amino)pyrimidin-4-yl)-3,4-dihydropyrrolo[1,2-a]pyrazin-1(2H)-one (1.2 g, yield: 58%).

Table 2 lists the compound of Example 2 and compounds that were prepared according to the procedures for Example 2 by using the corresponding intermediates and reagents under appropriate conditions that could be recognized by one skilled in the art.

TABLE 2

| Compound No. | STRUCTURE | Chemical Name | LCMS (M + H) | 1H NMR (400 MHz) |
|---|---|---|---|---|
| 5 | 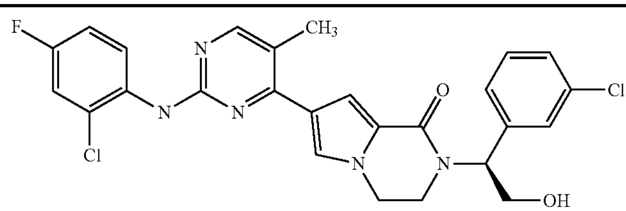 | (S)-7-(2-((2-chloro-4-fluorophenyl)amino)-5-methylpyrimidin-4-yl)-2-(1-(3-chlorophenyl)-2-hydroxyethyl)-3,4-dihydropyrrolo[1,2-a]pyrazin-1(2H)-one | 526.0 | $^1$H NMR (400 MHz CDCl$_3$) δ 8.23 (s, 1H), 8.14 (s, 1H), 7.81 (d, J = 7.6 Hz, 1H), 7.44 (s, 1H), 7.39 (s, 1H), 7.31 (m, 3H), 7.25-7.21 (m, 1H), 7.17 (m, 1H), 7.05 (t, J = 6.9 Hz, 1H), 5.89 (m, 1H), 4.30-4.17 (m, 4H), 3.73 (m, 1H), 3.40 (m, 1H), 2.34 (s, 3H) |
| 6 | 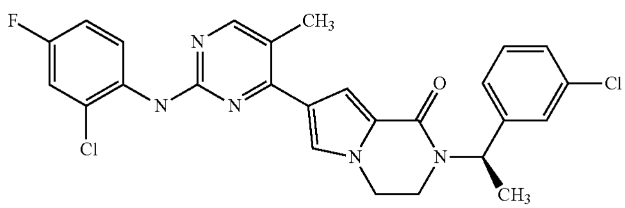 [SMILES: Cc1cnc(Nc2ccc(F)cc2Cl)nc1-c1cc2n(c1)CCN([C@H](C)c1cccc(Cl)c1)C2=O] | (R)-7-(2-((2-chloro-4-fluorophenyl)amino)-5-methylpyrimidin-4-yl)-2-(1-(3-chlorophenyl)ethyl)-3,4-dihydropyrrolo[1,2-a]pyrazin-1(2H)-one | 510.3 | $^1$H NMR (400 MHz, CDCl3) δ 8.53 (dd, J = 9.2, 5.6 Hz, 1H), 8.22 (s, 1H), 7.51 (s, 1H), 7.43 (s, 1H), 7.37 (s, 1H), 7.29 (d, J = 5.3 Hz, 3H), 7.14 (d, J = 8.6 Hz, 1H), 7.03 (t, J = 8.5 Hz, 1H), 6.17 (q, J = 6.9 Hz, 1H), 4.20-4.09 (m, 2H), 3.58 (m, 1H), 3.26 (m, 1H), 2.41 (s, 3H), 1.59 (d, J = 6.5 Hz, 3H). |

TABLE 2-continued

| Compound No. | STRUCTURE | Chemical Name | LCMS (M + H) | 1H NMR (400 MHz) |
|---|---|---|---|---|
| 7 | 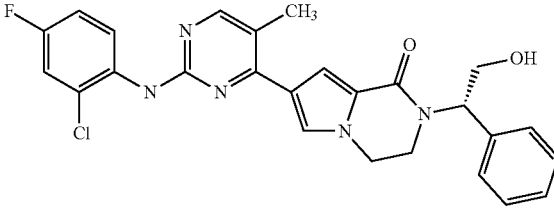 | (S)-8-(2-((2-chloro-4-fluorophenyl)amino)-5-methylpyrimidin-4-yl)-2-(1-(3-chlorophenyl)-2-hydroxyethyl)-2,3,4,5-tetrahydro-1H-pyrrolo[1,2-a][1,4]diazepin-1-one | 540.0 | ¹H NMR (400 MHz, CDCl₃) δ 8.53 (dd, J = 9.1, 5.7 Hz, 1H), 8.21 (s, 1H), 7.42 (s, 2H), 7.37 (s, 1H), 7.31 (m, 3H), 7.14 (d, J = 7.8 Hz, 1H), 7.05 (t, J = 8.3 Hz, 1H), 5.77 (dd, J = 9.0, 4.5 Hz, 1H), 4.29-4.05 (m, 4H), 3.31 (dd, J = 13.5, 6.8 Hz, 2H), 2.92 (s, 1H), 2.40 (s, 3H), 2.06 (dd, J = 13.0, 6.5 Hz, 1H), 1.71-1.62 (m, 1H). |
| 8 | 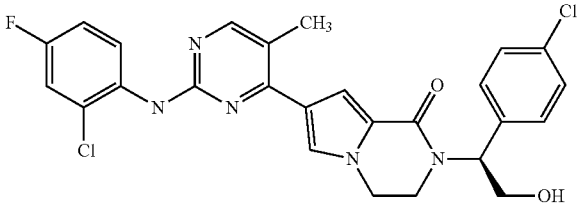 [SMILES: Cc1cnc(Nc2ccc(F)cc2Cl)nc1-c1cc2n(c1)CCN([C@H](CO)c1ccc(Cl)cc1)C2=O] | (S)-7-(2-((2-chloro-4-fluorophenyl)amino)-5-methylpyrimidin-4-yl)-2-(1-(4-chlorophenyl)-2-hydroxyethyl)-3,4-dihydropyrrolo[1,2-a]pyrazin-1(2H)-one | 526.0 | ¹H NMR (400 MHz, CDCl3) δ 8.52 (dd, J = 9.2, 5.7 Hz, 1H), 8.20 (s, 1H), 7.48 (s, 1H), 7.38-7.28 (m, 5H), 7.15 (dd, J = 7.9, 2.8 Hz, 1H), 7.10-7.00 (m, 1H), 5.89 (dd, J = 8.6, 4.8 Hz, 1H), 4.29-4.13 (m, 3H), 4.06-3.98 (m, 1H), 3.71 (m, 1H), 3.38 (m, 1H), 2.34 (s, 3H). |
| 9 | 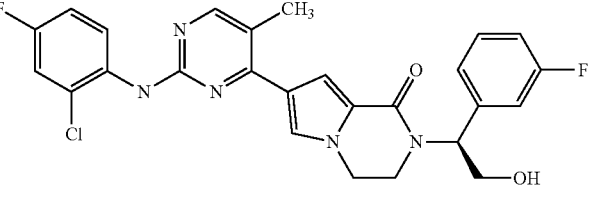 | (S)-7-(2-((2-chloro-4-fluorophenyl)amino)-5-methylpyrimidin-4-yl)-2-(1-(3-fluorophenyl)-2-hydroxyethyl)-3,4-dihydropyrrolo[1,2-a]pyrazin-1(2H)-one | 510.0 | ¹H NMR (400 MHz, (CDCl3) δ 8.52 (dd, J = 9.2, 5.7 Hz, 1H), 8.19 (s, 1H), 7.49 (d, J = 1.6 Hz, 1H), 7.34-7.30 (m, 2H), 7.15 (dd, J = 8.0, 3.0 Hz, 2H), 7.05 (m, 3H), 5.92 (dd, J = 8.5, 4.9 Hz, 1H), 4.15 (m, 4H), 3.73 (m, 1H), 3.40 (m, 1H), 2.34 (s, 3H). |
| 10 | 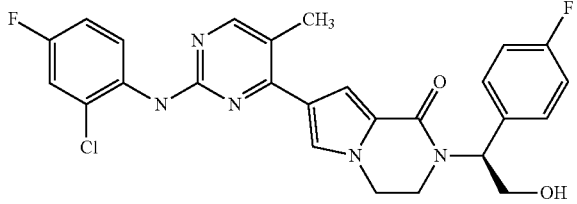 [SMILES: Cc1cnc(Nc2ccc(F)cc2Cl)nc1-c1cc2n(c1)CCN([C@H](CO)c1ccc(F)cc1)C2=O] | (S)-7-(2-((2-chloro-4-fluorophenyl)amino)-5-methylpyrimidin-4-yl)-2-(1-(4-fluorophenyl)-2-hydroxyethyl)-3,4-dihydropyrrolo[1,2-a]pyrazin-1(2H)-one | 510.2 | ¹H NMR (400 MHz, CDCl3) δ 8.52 (dd, J = 9.2, 5.7 Hz, 1H), 8.20 (s, 1H), 7.49 (d, J = 1.6 Hz, 1H), 7.41-7.26 (m, 4H), 7.15 (dd, J = 8.1, 2.9 Hz, 1H), 7.06 (m, 2H), 5.91 (dd, J = 8.7, 4.9 Hz, 1H), 4.26 (m, 1H), 4.22-4.13 (m, 2H), 4.03 (m, 2H), 3.71 m, 1H), 3.41-3.33 (m, 1H), 2.35 (s, 3H). |
| 11 | 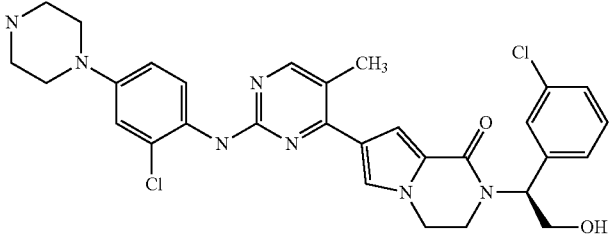 | (S)-7-(2-((2-chloro-4-(piperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one | 592.5 | ¹H NMR (400 MHz, DMSO) δ 8.2 (s, 1H), 8.1 (s, 1H), 7.71-7.56 (m, 2H), 7.44-7.28 (m, 4H), 7.21 (s, 1H), 7.05 (s, 1H), 6.96 (m, 1H), 5.67 (m, 1H), 5.13 (m, 1H), 4.21 (m, 2H), 3.95 (s, 2H), 3.72 (s, 1H), 3.29 (m, 5H), 3.06 (m, 4H), 2.28 (s, 3H). |

TABLE 2-continued

| Compound No. | STRUCTURE | Chemical Name | LCMS (M + H) | 1H NMR (400 MHz) |
|---|---|---|---|---|
| 12 | 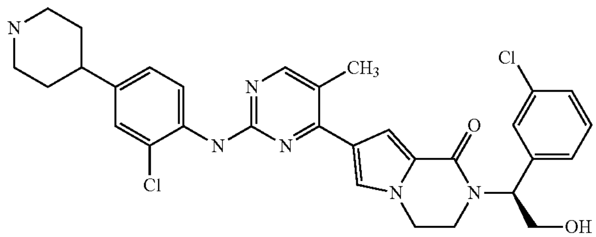 [SMILES: Cc1cnc(Nc2ccc(N3CCNCC3)cc2Cl)nc1-c1cc2n(c1)CCN([C@H](CO)c1cccc(Cl)c1)C2=O] | (S)-7-(2-((2-chloro-4-(piperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one | 591.4 | $^1$H NMR (400 MHz, DMSO) δ 8.21 (m, 2H), 7.97 (m, 1H), 7.65 (s, 1H), 7.41-7.18 (m, 6H), 5.69 (m, 1H), 5.13 (m, 1H), 4.26-4.25 (m, 2H), 4.19 (m, 2H), 3.96 (m, 2H), 3.7 (m, 2H), 3.05 (m, 2H), 2.61 (m, 3H), 2.31 (s, 3H), 1.75 (m, 2H), 1.54 (m, 2H). |
| 13 | 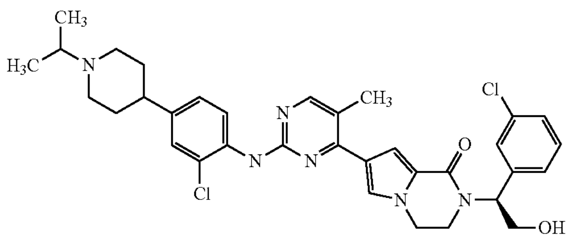 [SMILES: Cc1cnc(Nc2ccc(C3CCN(C(C)C)CC3)cc2Cl)nc1-c1cc2n(c1)CCN([C@H](CO)c1cccc(Cl)c1)C2=O] | (S)-7-(2-((2-chloro-4-(1-isopropylpiperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one | 633.4 | $^1$H NMR (400 MHz, DMSO) δ 10.35-10.25 (m, 1H), 8.29 (m, 1H), 8.22 (m, 1H), 8.02 (m, 1H), 7.66 (s, 1H), 7.44-7.19 (m, 6H), 5.68 (m, 1H), 5.13 (s, 1H), 4.22 (m, 2H), 3.95 (m, 2H), 3.73 (s, 1H), 3.47 (s, 4H), 3.02 (m, 2H), 2.84 (m, 1H), 2.31 (s, 3H), 2.01 (m, 4H), 1.28 (d, 6H). |
| 14 | 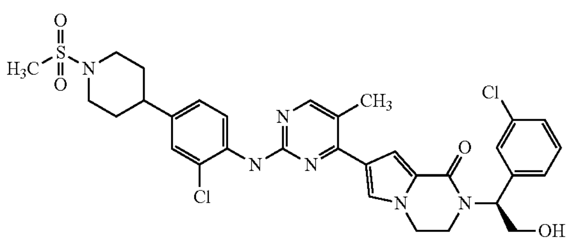 [SMILES: Cc1cnc(Nc2ccc(C3CCN(S(C)(=O)=O)CC3)cc2Cl)nc1-c1cc2n(c1)CCN([C@H](CO)c1cccc(Cl)c1)C2=O] | (S)-7-(2-((2-chloro-4-(1-(methylsulfonyl)piperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one | 669.1 | $^1$H NMR (400 MHz, DMSO) δ 8.22 (m, 2H), 7.98 (m, 1H), 7.65 (s, 1H), 7.46-7.21 (m, 7H), 5.69 (m, 1H), 5.11 (m, 1H), 4.27 (m, 1H), 4.16 (m, 1H), 3.95 (m, 2H), 3.65 (m, 3H), 3.42 (m, 1H), 2.89 (s, 3H), 2.79 (m, 2H), 2.63 (m, 1H), 2.31 (s, 3H), 1.87 (m, 2H), 1.69 (m, 2H). |
| 15 | 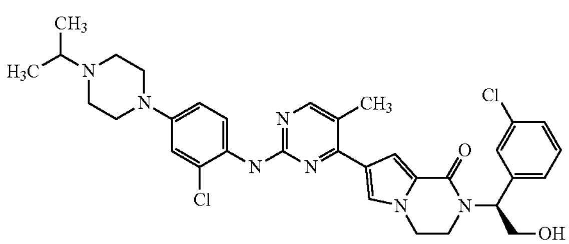 | (S)-7-(2-((2-chloro-4-(4-isopropylpiperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one | 634.2 | $^1$H NMR (400 MHz, DMSO) δ 8.19 (s, 1H), 8.13 (s, 1H), 7.60 (m, 2H), 7.43-7.29 (m, 4H), 7.21 (s, 1H), 7.00 (m, 1H), 6.93 (m, 1H), 5.67 (m, 1H), 5.11 (m, 1H), 4.20 (m, 1H), 4.17 (m, 1H), 3.95 (m, 3H), 3.72 (m, 2H), 3.13 (m, 4H), 2.65 (m, 4H), 2.27 (s, 3H), 1.16 (d, 6H). |
| 16 | 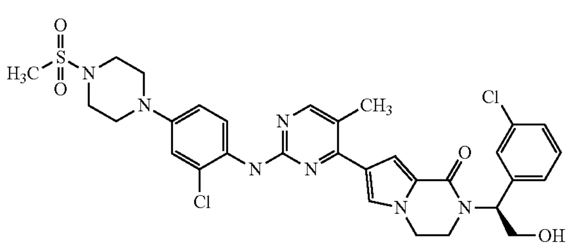 [SMILES: Cc1cnc(Nc2ccc(N3CCN(S(C)(=O)=O)CC3)cc2Cl)nc1-c1cc2n(c1)CCN([C@H](CO)c1cccc(Cl)c1)C2=O] | (S)-7-(2-((2-chloro-4-(4-(methylsulfonyl)piperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one | 670.2 | Unavailable. |

TABLE 2-continued

| Compound No. | STRUCTURE | Chemical Name | LCMS (M + H) | 1H NMR (400 MHz) |
|---|---|---|---|---|
| 17 | 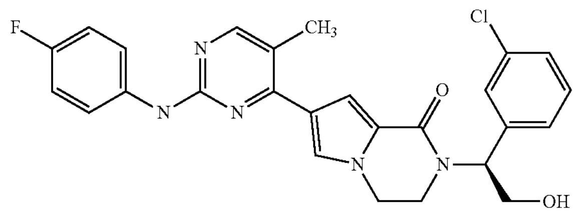 [SMILES: Cc1cnc(Nc2ccc(F)cc2)nc1-c1cc2n(c1)CCN([C@H](CO)c1cccc(Cl)c1)C2=O] | (S)-2-(1-(3-chlorophenyl)-2-hydroxyethyl)-7-(2-((4-fluorophenyl)amino)-5-methylpyrimidin-4-yl)-3,4-dihydropyrrolo[1,2-a]pyrazin-1(2H)-one | 492.2 | $^1$H NMR (400 MHz, CDCl$_3$) δ 8.14 (s, 1H), 7.58 (dd, J = 8.9, 4.7 Hz, 2H), 7.47 (s, 1H), 7.34 (s, 1H, 7.30 (d, J = 5.6 Hz, 2H), 7.25-7.23 (m, 1H), 7.10 (s, 1H), 7.04 (t, J = 8.7 Hz, 2H), 5.91 (dd, J = 8.6, 5.0 Hz, 1H), 4.26 (m, 1H), 4.16 (m, 2H), 4.04-3.97 (m, 1H), 3.76-3.68 (m., 1H), 3.40 (m, 1H), 2.30 (s, 3H). |
| 18 | 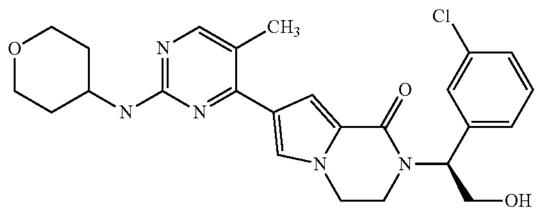 [SMILES: Cc1cnc(NC2CCOCC2)nc1-c1cc2n(c1)CCN([C@H](CO)c1cccc(Cl)c1)C2=O] | S)-2-(1-(3-chlorophenyl)-2-hydroxyethyl)-7-(5-methyl-2-((tetrahydro-2H-pyran-4-yl)amino)pyrimidin-4-yl)-3,4-dihydropyrrolo[1,2-a]pyrazin-1(2H)-one | 482.2 | $^1$H NMR (400 MHz, CDCl$_3$) δ 8.07 (s, 1H), 7.47 (d, J = 1.5 Hz, 1H), 7.35 (m, 2H), 7.33-7.29 (m, 2H), 7.25-7.23 (m, 1H), 5.87 (dd, J = 8.3, 5.0 Hz, 1H), 4.85 (d, J = 7.8 Hz, 1H), 4.30-3.90 (m, 5H), 3.77-3.67 (m, 2H), 3.56 (m, 2H), 3.46-3.36 (m, 2H), 2.31 (s, 3H), 2.06 (m, 2H), 1.52 (m, 2H). |
| 19 | 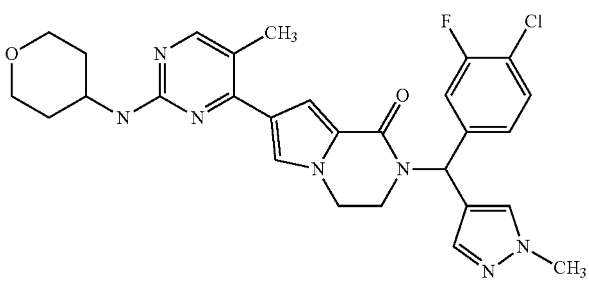 [SMILES: Cc1cnc(NC2CCOCC2)nc1-c1cc2n(c1)CCN(C(c1ccc(Cl)c(F)c1)c1cnn(C)c1)C2=O] | 2-((4-chloro-3-fluorophenyl)(1-methyl-1H-pyrazol-4-yl)methyl)-7-(5-methyl-2-((tetrahydro-2H-pyran-4-yl)amino)pyrimidin-4-yl)-3,4-dihydropyrrolo[1,2-a]pyrazin-1(2H)-one | 550.6 | $^1$H NMR (400 MHz, CDCl$_3$) δ 8.07 (s, 1H), 7.46 (s, 1H), 7.42 (d, J = 4.8 Hz, 1H), 7.40-7.35 (m, 2H), 7.15 (m, 3H), 4.84 (d, J = 7.7 Hz, 1H, 4.18 (m, 2H), 4.05 (m, 1H), 3.98 (m, 2H), 3.92 (s, 3H), 3.56-3.48 (m, 4H), 2.31 (s, 3H), 2.05 (m, 2H), 1.54 (m, 2H). |
| 20 | 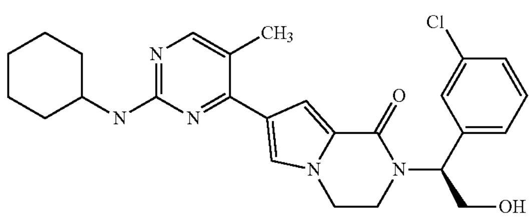 [SMILES: Cc1cnc(NC2CCCCC2)nc1-c1cc2n(c1)CCN([C@H](CO)c1cccc(Cl)c1)C2=O] | (S)-2-(1-(3-chlorophenyl)-2-hydroxyethyl)-7-(2-(cyclohexylamino)-5-methylpyrimidin-4-yl)-3,4-dihydropyrrolo[1,2-a]pyrazin-1(2H)-one | 480.2 | $^1$H NMR (400 MHz, CDCl$_3$) δ 8.05 (s, 1H), 7.47 (s, 1H), 7.35 (m, 2H), 7.30 (m, 3H), 5.85 (m, 1H), 4.83 (m, 1H), 4.23 (m, 1H), 4.14 (m, 2H), 4.10-4.03 (m, 1H), 3.83 (m, 1H), 3.71 (m, 1H), 3.41 (m, 1H), 2.30 (s, 3H), 2.04 (s, 1H), 1.80-1.55 (m, 10H). |
| 21 | 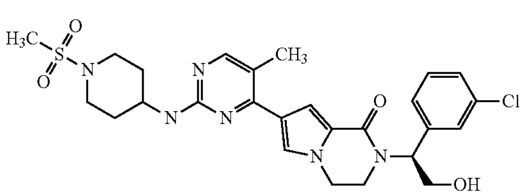 [SMILES: Cc1cnc(NC2CCN(S(C)(=O)=O)CC2)nc1-c1cc2n(c1)CCN([C@H](CO)c1cccc(Cl)c1)C2=O] | (S)-2-(1-(3-chlorophenyl)-2-hydroxyethyl)-7-(5-methyl-2-((1-(methylsulfonyl)piperidin-4-yl)amino)pyrimidin-4-yl)-3,4-dihydropyrrolo[1,2-a]pyrazin-1(2H)-one | 559.4 | $^1$H NMR (400 MHz, CDCl$_3$) δ 8.07 (s, 1H), 7.50 (s, 1H), 7.33 (m, 3H), 7.24-7.15 (m, 2H), 5.87-5.83 (m, 1H), 4.85 (m, 1H), 4.28-3.86 (m, 4 H), 3.72 (m, 3H), 3.43 (m, 2H), 2.96 (m, 2H), 2.81 (s, 3H), 2.32 (s, 3H), 2.20 (m, 2H), 2.00 (m, 2H). |

EXAMPLE 4: COLO205 CELL PROLIFERATION ASSAY

Compounds of this disclosure were tested for the inhibition of ERK2 by a Colo205 cell proliferation assay commonly known as MTT assay. In this assay, a complete media was prepared by adding 10% fetal bovine serum to RPMI-1640 medium (Life technology). Colon cancer cells (Colo205 cell line) were added to each of 88 wells of a 96 well plate at a seeding density of 5,000 cells/well/90 μL. The cells were allowed to attach to the plate by incubating at 37'C for 24 hours. The compound was dissolved in DMSO (SIGMA). A solution of test compound was prepared in complete media by serial dilution to obtain the following concentrations: 500 µM, 150 µM, 50 µM, 15 µM, 5 µM, 1.5 µM, 0.5 µM, 0.15 µM and 0.05 µM. The test compound solution (10 µL) is added to each of 80 cell-containing wells. The final concentrations of the compound were following: 50 µM, 15 µM, 5 µM, 1.5 µM, 0.5 µM, 0.15 µM, 0.05 µM, 0.015 µM and 0.005 µM. The final concentration of DMSO is 0.5%. To the 8 remaining cell-containing wells, only complete media (containing 0.5% DMSO) was added to form a control group in order to measure maximal proliferation. To the remaining 8 empty wells, complete media was added to for a vehicle control group in order to measure background. The plates were incubated at 37° C. for 72 hours. 10 µL WST-8 solution (DOJINDO, Cell Counting KIT-8) was added to each well. The plates were further incubated at 37° C. for 2 hours, and then read for the absorbance using a microplate reader at 450 nm.

Subjected to this cell proliferation assay, Compounds 1 and 4-21 was found to have cell growth inhibition $IC_{50}$ value below 15.0 µM, such as ranging from 0.122 µM to 10.6 µM.

EXAMPLE 5: ENZYMATIC ASSAY

Compounds were tested in a LanthaScreen™ time-resolved fluorescence energy transfer (TR-FRET) enzymatic assay from Invitrogen. The assay used human ERK2 (Mitogen Activated Kinase 1, Invitrogen, Cat. PV3311) recombinantly expressed as GST-tagged full-length protein purified from *E. coli* and activated in vitro with MAP2K1. The substrate was a recombinant truncated version (residues 19-96) of ATF2 fused with Green Fluorescent Protein (Invitrogen, Cat. PV4445). Test compounds were prepared and diluted in DMSO in 3-fold serial dilutions to 100× of the final testing concentrations. The compounds were then further diluted to 4× by the kinase reaction buffer (Invitrogen, Cat. PV3189). The enzymatic reaction for compound testing was performed in a white 384-well polypropylene plate (Packard, Cat. 6005214) with a total reaction volume of 10 µl containing 20 ng/ml ERK2, 400 nM substrate, and 5 µM ATP that is around its $K_m$. The assay started with loading 2.5 µl of ERK2 diluted in kinase reaction buffer to wells, followed by addition of equal volume of 4× compounds for 15-min incubation at the room temperature for pre-treatment. The enzymatic reaction was initiated by addition of 5 µl of mixture of the substrate and ATP prepared in kinase reaction buffer. After one hour reaction, 10 µl mixture of EDTA (final 10 mM) and terbium-labeled anti-pATF2 (pThr71) antibody (final 2 nM) (Invitrogen, Cat. PV4451) prepared in TR-FRET antibody dilution buffer (Invitrogen, Cat. PV3574) was added to stop the enzymatic reaction and produce TR-FRET signals. After 30 minutes of incubation at room temperature, the plate was read in Tecan Infinite F200 Pro with the following settings: Excitation 340 nm (30)/Emission1 495 nm (10)/Emission2 520 nm (25). The TR-FRET values were dimensionless numbers that were calculated as the ratio of the acceptor (Green Fluorescent Protein) signal to the donor (Terbium) signal. Percent of control was calculated as the percentage of compound-treated vs 1% DMSO vehicle-treated. The dose-response curves were generated and the $IC_{50}$ s were calculated by nonlinear sigmoid curve fitting using GraphPad Prism.

Subjected to this enzymatic assay, Compounds 1-21 was found to have ERK2 $IC_{50}$ value below 150 nM, such as in the range of 0.34 nM to 128 nM.

What is claimed is:
1. A compound of formula I:

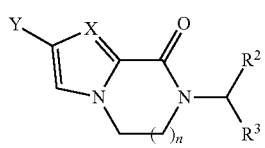

and/or a pharmaceutically acceptable salt thereof;
wherein:
X is C—R, wherein R is hydrogen, halo, alkyl, haloalkyl, —CN, or alkoxy;
Y is a monocyclic or 6,5-fused bicyclic aryl or heteroaryl optionally substituted with at least one group selected from halo, alkyl, alkenyl, alkoxy, alkynyl, aryl, cycloalkyl, heteroaryl, heterocyclyl, —OH, —CN, —COOR$_a$, —SO$_2$NR$_a$R$_b$, —CONR$_a$R$_b$, and —NR$_a$R$_b$, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONR$_a$R$_b$, and —NR$_a$R$_b$;
R$^2$ is hydrogen, aryl, —CONR$_a$R$_b$, alkyl, alkoxy, —COOR$_a$, cycloalkyl, heteroaryl, or heterocyclyl;
R$^3$ is hydrogen, alkyl, aryl, cycloalkyl, alkenyl, alkynyl, alkoxy, heteroaryl, or heterocyclyl;
wherein each of the alkyl, alkoxy, aryl, cycloalkyl, alkenyl, alkynyl, heteroaryl, and heterocyclyl for R$^2$ and/or R$^3$ is optionally substituted with at least one group selected from —OH, alkoxy, halo, and alkyl;
R$_a$ and R$_b$ are independently H, alkyl, aryl, cycloalkyl, heterocyclyl, or heteroaryl, wherein each of the alkyl, aryl, cycloalkyl, heterocyclyl, and heteroaryl is optionally substituted with at least one group selected from halo, alkyl, haloalkyl, alkoxy, —C(O)alkyl, —SO$_2$-alkyl, —OH, cycloalkyl, and heterocyclyl optionally substituted with at least one group selected from alkyl, —C(O)-alkyl, and —SO$_2$-alkyl; or
R$_a$ and R$_b$, together with the atoms to which they are attached, form a heterocyclic ring optionally substituted with at least one group selected from halo, alkyl, haloalkyl, alkoxy, and —OH; and
n is 1.

2. The compound of claim 1, and/or a pharmaceutically acceptable salt thereof, wherein X is C—R, and R is H, halo, alkyl, haloalkyl, —CN, or alkoxy.

3. The compound of claim 1, and/or a pharmaceutically acceptable salt thereof, wherein Y is a monocyclic or 6,5-fused bicyclic aryl optionally substituted with at least one group selected from halo, alkyl, alkenyl, alkoxy, alkynyl, aryl, cycloalkyl, heteroaryl, heterocyclyl, —OH, —N, —COOR$_a$, —SO$_2$NR$_a$R$_b$, —CONR$_a$R$_b$, and —NR$_a$R$_b$, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONR$_a$R$_b$, and —NR$_a$R$_b$, wherein R$_a$ and R$_b$ are as defined in claim 1.

4. The compound of claim 3, and/or a pharmaceutically acceptable salt thereof, wherein Y is 1H-indenyl or 1,2-dihydronaphthalene, optionally substituted with at least one group selected from halo, alkyl, H, alkenyl, alkoxy, alkynyl, aryl, cycloalkyl, heteroaryl, heterocyclyl, —OH, —CN, —COOR$_a$, —SO$_2$NR$_a$R$_b$, —CONR$_a$R$_b$, and —NR$_a$R$_b$, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONR$_a$R$_b$, and —NR$_a$R$_b$, and wherein R$_a$ and R$_b$ are as defined in claim 1.

5. The compound of claim 1, and/or a pharmaceutically acceptable salt thereof, wherein Y is a monocyclic or 6,5-fused bicyclic heteroaryl optionally substituted with at least one group selected from halo, alkyl, alkenyl, alkoxy, alkynyl, aryl, cycloalkyl, heteroaryl, heterocyclyl, —OH, —CN, —COOR$_a$, —SO$_2$NR$_a$R$_b$, —CONR$_a$R$_b$, and —NR$_a$R$_b$, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONR$_a$R$_b$, and —NR$_a$R$_b$, and wherein R$_a$ and R$_b$ are as defined in claim 1.

6. The compound of claim 5, and/or a pharmaceutically acceptable salt thereof, wherein Y is 1H-pyrazolo[3,4-b]pyridinyl, 1H-pyrrolo[2,3-b]pyridinyl, or pyrimidinyl optionally substituted with at least one group selected from halo, alkyl, alkenyl, alkoxy, alkynyl, aryl, cycloalkyl, heteroaryl, heterocyclyl, —OH, —CN, —COOR$_a$, —SO$_2$NR$_a$R$_b$, —CONR$_a$R$_b$, and —NR$_a$R$_b$, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONR$_a$R$_b$, and —NR$_a$R$_b$, and wherein R$_a$ and R$_b$ are as defined in claim 1.

7. The compound of claim 6, and/or a pharmaceutically acceptable salt thereof, wherein Y is pyrimidinyl optionally substituted with at least one group selected from halo, alkyl, alkenyl, alkoxy, alkynyl, aryl, cycloalkyl, heteroaryl, heterocyclyl, —OH, —CN, —COOR$_a$, —SO$_2$NR$_a$R$_b$, —CONR$_a$R$_b$, and —NR$_a$R$_b$, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONR$_a$R$_b$, and —NR$_a$R$_b$, and wherein R$_a$ and R$_b$ are as defined in claim 1.

8. The compound of claim 7, and/or a pharmaceutically acceptable salt thereof, wherein Y is pyrimidinyl optionally substituted with at least one group selected from halo, alkyl, and —NR$_a$R$_b$, wherein R$_a$ and R$_b$ are as defined in claim 1.

9. The compound of claim 1, and/or a pharmaceutically acceptable salt thereof, wherein R$^2$ is aryl, cycloalkyl, heteroaryl, or heterocyclyl, wherein each of the aryl, cycloalkyl, heteroaryl, and heterocyclyl is optionally substituted with at least one group selected from —OH, alkoxy, halo, and alkyl.

10. The compound of claim 9, and/or a pharmaceutically acceptable salt thereof, wherein R$^2$ is aryl optionally substituted with at least one group selected from —OH, alkoxy, halo, and alkyl.

11. The compound of claim 1, and/or a pharmaceutically acceptable salt thereof, wherein R$^3$ is alkyl, aryl, or heteroaryl, wherein each of the alkyl, aryl, and heteroaryl is optionally substituted with at least one group selected from —OH, alkoxy, halo, and alkyl.

12. The compound of claim 11, and/or a pharmaceutically acceptable salt thereof, wherein R$^3$ is alkyl optionally substituted with at least one group selected from —OH, alkoxy, and halo.

13. The compound of claim 1, and/or a pharmaceutically acceptable salt thereof, wherein the carbon to which R$^2$ and R$^3$ are attached has the following chiral orientation:

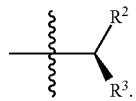

14. The compound of claim 1, and/or a pharmaceutically acceptable salt thereof, wherein the carbon to which R$^2$ and R$^3$ are attached has the following chiral orientation:

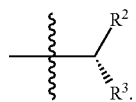

15. The compound of claim 1, and/or a pharmaceutically acceptable salt thereof, which is a compound of formula II and/or a pharmaceutically acceptable salt thereof:

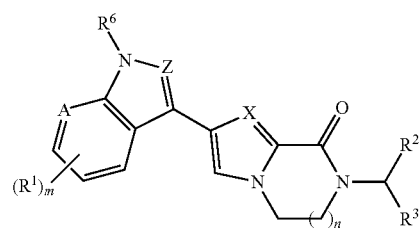

II wherein:
X, R$^2$ and R$^3$ are as defined in claim 1,
Z is N or C—R$^5$, wherein R$^5$ is H or alkyl optionally substituted with at least one group selected from alkoxy and halo;
R$^6$ is H or alkyl optionally substituted with at least one group selected from alkoxy and halo;
A is N or C—R$^7$, wherein R$^7$ is H or alkyl optionally substituted with at least one group selected from alkoxy and halo;
m is 1 or 2;
n is 1;
R$^1$ is independently halo, alkyl, alkenyl, alkoxy, alkynyl, aryl, cycloalkyl, heteroaryl, heterocyclyl, —OH, —CN, —COOR$_a$, —SO$_2$NR$_a$R$_b$, —CONR$_a$R$_b$, or —NR$_a$R$_b$, wherein each of the group alkyl, alkenyl, alkoxy, alkynyl, aryl, cycloalkyl, heteroaryl and heterocyclyl is optionally substituted with at least one group selected from alkoxy, alkyl, halo, OH, —CN, —COOR$_a$, —SO$_2$NR$_a$R$_b$, —CONR$_a$R$_b$, and —NR$_a$R$_b$;
R$_a$ and R$_b$ are as defined in claim 1.

16. The compound of claim 15, and/or a pharmaceutically acceptable salt thereof, wherein Z is N.

17. The compound of claim 15, and/or a pharmaceutically acceptable salt thereof, wherein A is N.

18. The compound of claim 15, and/or a pharmaceutically acceptable salt thereof, wherein X is C—R and R is H or alkyl.

19. The compound of claim 1, and/or a pharmaceutically acceptable salt thereof, which is a compound of formula III and/or a pharmaceutically acceptable salt thereof:

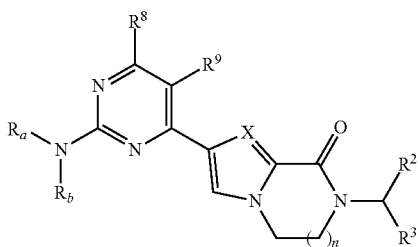

wherein:
X, R², and R³ are as defined in claim 1;
n is 1;
R⁸ and R⁹ are independently H or alkyl optionally substituted with at least one group selected from alkoxy and halo;
R_a and R_b are as defined in claim 1.

20. The compound of claim 19, and/or a pharmaceutically acceptable salt thereof, wherein X is C—H.

21. The compound of claim 19, and/or a pharmaceutically acceptable salt thereof, wherein R⁸ is H and R⁹ is an alkyl.

22. The compound of claim 19, and/or a pharmaceutically acceptable salt thereof, wherein R_a is H, and R_b is a phenyl optionally substituted with at least one group selected from halo, alkyl, and heterocyclyl optionally substituted with at least one group selected from alkyl, —C(O)-alkyl, and —(SO)₂-alkyl.

23. The compound of claim 19, and/or a pharmaceutically acceptable salt thereof, wherein R₂ is aryl substituted with at least one group selected from halo and alkyl.

24. The compound of claim 19, and/or a pharmaceutically acceptable salt thereof, wherein R₃ is alkyl optionally substituted with —OH.

25. A pharmaceutical composition, comprising a compound of claim 1, and/or a pharmaceutically acceptable salt, and a pharmaceutically acceptable carrier.

26. A method of treating cancer in a patient, comprising administering to the patient in recognized need of such treatment, an effective amount of a pharmaceutical composition comprising a compound of claim 1, and/or a pharmaceutically acceptable salt thereof, and a pharmaceutically acceptable carrier.

27. The method of claim 26, wherein the cancer is selected from colon cancer, gastric cancer, leukemia, lymphoma, melanoma, and pancreatic cancer.

28. A compound selected from
(S)-2-(1-(3-chloro-4-fluorophenyl)-2-hydroxyethyl)-7-(5-phenyl-1H-pyrazolo[3,4-b]pyridin-3-yl)-3,4-dihydropyrrolo[1,2-a]pyrazin-1(2H)-one;
(R)-2-(1-(3-chloro-4-fluorophenyl)-2-hydroxyethyl)-7-(5-phenyl-1H-pyrazolo[3,4-b]pyridin-3-yl)-3,4-dihydropyrrolo[1,2-a]pyrazin-1(2H)-one;
a mixture of (S)- and (R)-2-(1-(3-chloro-4-fluorophenyl)-2-hydroxyethyl)-7-(5-phenyl-1H-pyrazolo[3,4-b]pyridin-3-yl)-3,4-dihydropyrrolo[1,2-a]pyrazin-1(2H)-one;
(R)-2-(1-(3-chlorophenyl)ethyl)-7-(5-phenyl-1H-pyrrolo[2,3-b]pyridin-3-yl)-3,4-dihydropyrrolo[1,2-a]pyrazin-1(2H)-one;
(S)-2-(1-(3-chlorophenyl)ethyl)-7-(5-phenyl-1H-pyrrolo[2,3-b]pyridin-3-yl)-3,4-dihydropyrrolo[1,2-a]pyrazin-1(2H)-one;
a mixture of (R)- and (S)-2-(1-(3-chlorophenyl)ethyl)-7-(5-phenyl-1H-pyrrolo[2,3-b]pyridin-3-yl)-3,4-dihydropyrrolo[1,2-a]pyrazin-1(2H)-one;
(R)-2-(1-(3-chlorophenyl)ethyl)-7-(5-phenyl-1H-pyrazolo[3,4-b]pyridin-3-yl)-3,4-dihydropyrrolo[1,2-a]pyrazin-1(2H)-one;
(S)-2-(1-(3-chlorophenyl)ethyl)-7-(5-phenyl-1H-pyrazolo[3,4-b]pyridin-3-yl)-3,4-dihydropyrrolo[1,2-a]pyrazin-1(2H)-one;
a mixture of (R)- and (S)-2-(1-(3-chlorophenyl)ethyl)-7-(5-phenyl-1H-pyrazolo[3,4-b]pyridin-3-yl)-3,4-dihydropyrrolo[1,2-a]pyrazin-1(2H)-one;
(S)-2-(1-(3-chlorophenyl)-2-hydroxyethyl)-7-(5-phenyl-1H-pyrrolo[2,3-b]pyridin-3-yl)-3,4-dihydropyrrolo[1,2-a]pyrazin-1(2H)-one;
(R)-2-(1-(3-chlorophenyl)-2-hydroxyethyl)-7-(5-phenyl-1H-pyrrolo[2,3-b]pyridin-3-yl)-3,4-dihydropyrrolo[1,2-a]pyrazin-1(2H)-one;
a mixture of (R)- and (S)-2-(1-(3-chlorophenyl)-2-hydroxyethyl)-7-(5-phenyl-1H-pyrrolo[2,3-b]pyridin-3-yl)-3,4-dihydropyrrolo[1,2-a]pyrazin-1(2H)-one;
(S)-7-(2-((2-chloro-4-fluorophenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(R)-7-(2-((2-chloro-4-fluorophenyl)amino)-5-methylpyrimidin-4-yl)-2-(1-(3-chlorophenyl)-2-hydroxyethyl)-3,4-dihydropyrrolo[1,2-a]pyrazin-1(2H)-one;
a mixture of (R)- and (S)-7-(2((2-chloro-4-fluorophenyl)amino)-5-methylpyrimidin-4-yl)-2-(1-(3-chlorophenyl)-2-hydroxyethyl)-3,4-dihydropyrrolo[1,2-a]pyrazin-1(2H)-one;
(R)-7-(2-((2-chloro-4-fluorophenyl)amino)-5-methylpyrimidin-4-yl)-2-(1-(3-chlorophenyl)ethyl)-3,4-dihydropyrrolo[1,2-a]pyrazin-1(2H)-one;
(S)-7-(2-((2-chloro-4-fluorophenyl)amino)-5-methylpyrimidin-4-yl)-2-(1-(3-chlorophenyl)ethyl)-3,4-dihydropyrrolo[1,2-a]pyrazin-1(2H)-one;
a mixture of (R)- and (S)-7-(2-((2-chloro-4-fluorophenyl)amino)-5-methylpyrimidin-4-yl)-2-(1-(3-chlorophenyl)ethyl)-3,4-dihydropyrrolo[1,2-a]pyrazin-1(2H)-one;
(S)-7-(2-((2-chloro-4-fluorophenyl)amino)-5-methylpyrimidin-4-yl)-2-(1-(4-chlorophenyl)-2-hydroxyethyl)-3,4-dihydropyrrolo[1,2-a]pyrazin-1 (2H)-one;
(R)-7-(2-((2-chloro-4-fluorophenyl)amino)-5-methylpyrimidin-4-yl)-2-(1-(4-chlorophenyl)-2-hydroxyethyl)-3,4-dihydropyrrolo[1,2-a]pyrazin-1(2H)-one;
a mixture of (R)- and (S)-7-(2-((2-chloro-4-fluorophenyl)amino)-5-methylpyrimidin-4-yl)-2-(1-(4-chlorophenyl)-2-hydroxyethyl)-3,4-dihydropyrrolo[1,2-a]pyrazin-1(2H)-one;
(S)-7-(2-((2-chloro-4-fluorophenyl)amino)-5-methylpyrimidin-4-yl)-2-(1-(3-fluorophenyl)-2-hydroxyethyl)-3,4-dihydropyrrolo[1,2-a]pyrazin-1(2H)-one;
(R)-7-(2-((2-chloro-4-fluorophenyl)amino)-5-methylpyrimidin-4-yl)-2-(1-(3-fluorophenyl)-2-hydroxyethyl)-3,4-dihydropyrrolo[1,2-a]pyrazin-1(2H)-one;
A mixture of (R)- and (S)-7-(2-((2-chloro-4-fluorophenyl)amino)-5-methylpyrimidin-4-yl)-2-(1-(3-fluorophenyl)-2-hydroxyethyl)-3,4-dihydropyrrolo[1,2-a]pyrazin-1(2H)-one;
(S)-7-(2-((2-chloro-4-fluorophenyl)amino)-5-methylpyrimidin-4-yl)-2-(1-(4-fluorophenyl)-2-hydroxyethyl)-3,4-dihydropyrrolo[1,2-a]pyrazin-1(2H)-one;
(R)-7-(2-((2-chloro-4-fluorophenyl)amino)-5-methylpyrimidin-4-yl)-2-(1-(4-fluorophenyl)-2-hydroxyethyl)-3,4-dihydropyrrolo[1,2-a]pyrazin-1(2H)-one;

a mixture of (R)- and (S)-7-(2-((2-chloro-4-fluorophenyl)amino)-5-methylpyrimidin-4-yl)-2-(1-(4-fluorophenyl)-2-hydroxyethyl)-3,4-dihydropyrrolo[1,2-a]pyrazin-1(2H)-one;

(S)-7-(2-((2-chloro-4-(piperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

(R)-7-(2-((2-chloro-4-(piperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

a mixture of (R)- and (S)-7-(2-((2-chloro-4-(piperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

(S)-7-(2-((2-chloro-4-(piperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

(R)-7-(2-((2-chloro-4-(piperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

a mixture of (R)- and (S)-7-(2-((2-chloro-4-(piperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

(S)-7-(2-((2-chloro-4-(1-isopropylpiperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

(R)-7-(2-((2-chloro-4-(1-isopropylpiperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

a mixture of (R)- and (S)-7-(2-((2-chloro-4-(1-isopropylpiperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

(S)-7-(2-((2-chloro-4-(1-(methylsulfonyl)piperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

(R)-7-(2-((2-chloro-4-(1-(methylsulfonyl)piperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

a mixture of (R)- and (S)-7-(2-((2-chloro-4-(1-(methylsulfonyl)piperidin-4-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

(S)-7-(2-((2-chloro-4-(4-isopropylpiperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

(R)-7-(2-((2-chloro-4-(4-isopropylpiperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

a mixture of (R)- and (S)-7-(2-((2-chloro-4-(4-isopropylpiperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

(S)-7-(2-((2-chloro-4-(4-(methylsulfonyl)piperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

(R)-7-(2-((2-chloro-4-(4-(methylsulfonyl)piperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

a mixture of (R)- and (S)-7-(2-((2-chloro-4-(4-(methylsulfonyl)piperazin-1-yl)phenyl)amino)-5-methylpyrimidin-4-yl)-2-(1-(3-chlorophenyl)-2-hydroxyethyl)-3,4-dihydropyrrolo[1,2-a]pyrazin-1(2H)-one;

(S)-2-(1-(3-chlorophenyl)-2-hydroxyethyl)-7-(2-((4-fluorophenyl)amino)-5-methylpyrimidin-4-yl)-3,4-dihydropyrrolo[1,2-a]pyrazin-1(2H)-one;

(R)-2-(1-(3-chlorophenyl)-2-hydroxyethyl)-7-(2-((4-fluorophenyl)amino)-5-methylpyrimidin-4-yl)-3,4-dihydropyrrolo[1,2-a]pyrazin-1(2H)-one;

a mixture of (R)- and (S)-2-(1-(3-chlorophenyl)-2-hydroxyethyl)-7-(2-((4-fluorophenyl)amino)-5-methylpyrimidin-4-yl)-3,4-dihydropyrrolo[1,2-a]pyrazin-1(2H)-one;

(S)-2-(1-(3-chlorophenyl)-2-hydroxyethyl)-7-(5-methyl-2-((tetrahydro-2H-pyran-4-yl)amino)pyrimidin-4-yl)-3,4-dihydropyrrolo[1,2-a]pyrazin-1(2H)-one;

(R)-2-(1-(3-chlorophenyl)-2-hydroxyethyl)-7-(5-methyl-2-((tetrahydro-2H-pyran-4-yl)amino)pyrimidin-4-yl)-3,4-dihydropyrrolo[1,2-a]pyrazin-1(2H)-one;

a mixture of (R)- and (S)-2-(1-(3-chlorophenyl)-2-hydroxyethyl)-7-(5-methyl-2-((tetrahydro-2H-pyran-4-yl)amino)pyrimidin-4-yl)-3,4-dihydropyrrolo[1,2-a]pyrazin-1(2H)-one;

(R)-2-((4-chloro-3-fluorophenyl)(1-methyl-1H-pyrazol-4-yl)methyl)-7-(5-methyl-2-((tetrahydro-2H-pyran-4-yl)amino)pyrimidin-4-yl)-3,4-dihydropyrrolo[1,2-a]pyrazin-1(2H)-one;

(S)-2-((4-chloro-3-fluorophenyl)(1-methyl-1H-pyrazol-4-yl)methyl)-7-(5-methyl-2-((tetrahydro-2H-pyran-4-yl)amino)pyrimidin-4-yl)-3,4-dihydropyrrolo[1,2-a]pyrazin-1 (2H)-one;

a mixture of (R)- and (S)-2-((4-chloro-3-fluorophenyl)(1-methyl-1H-pyrazol-4-yl)methyl)-7-(5-methyl-2-((tetrahydro-2H-pyran-4-yl)amino)pyrimidin-4-yl)-3,4-dihydropyrrolo[1,2-a]pyrazin-1(2H)-one;

(S)-2-(1-(3-chlorophenyl)-2-hydroxyethyl)-7-(2-(cyclohexylamino)-5-methylpyrimidin-4-yl)-3,4-dihydropyrrolo[1,2-a]pyrazin-1(2H)-one;

(R)-2-(1-(3-chlorophenyl)-2-hydroxyethyl)-7-(2-(cyclohexylamino)-5-methylpyrimidin-4-yl)-3,4-dihydropyrrolo[1,2-a]pyrazin-1(2H)-one;

a mixture of (R)- and (S)-2-(1-(3-chlorophenyl)-2-hydroxyethyl)-7-(2-(cyclohexylamino)-5-methylpyrimidin-4-yl)-3,4-dihydropyrrolo[1,2-a]pyrazin-1(2H)-one;

(S)-2-(1-(3-chlorophenyl)-2-hydroxyethyl)-7-(5-methyl-2-((1-(methylsulfonyl)piperidin-4-yl)amino)pyrimidin-4-yl)-3,4-dihydropyrrolo[1,2-a]pyrazin-1(2H)-one;

(R)-2-(1-(3-chlorophenyl)-2-hydroxyethyl)-7-(5-methyl-2-((1-(methylsulfonyl)piperidin-4-yl)amino)pyrimidin-4-yl)-3,4-dihydropyrrolo[1,2-a]pyrazin-1(2H)-one; and a mixture of (R)- and (S)-2-(1-(3-chlorophenyl)-2-hydroxyethyl)-7-(5-methyl-2-((1-(methylsulfonyl)piperidin-4-yl)amino)pyrimidin-4-yl)-3,4-dihydropyrrolo[1,2-a]pyrazin-1(2H)-one, and/or a pharmaceutically acceptable salt thereof.

29. The compound of claim 28, and/or a pharmaceutically acceptable salt thereof, which is selected from (R)-7-(2-((2- chloro-4-fluorophenyl)amino)-5-methylpyrimidin-4-yl)-2-(1-(3-chlorophenyl)-2-hydroxyethyl)-3,4-dihydropyrrolo[1,2-a]pyrazin-1(2H)-one, (S)-7-(2-((2-chloro-4-fluorophenyl)amino)-5-methylpyrimidin-4-yl)-2-(1-(3-chlorophenyl)-2-hydroxyethyl)-3,4-dihydropyrrolo[1,2-a]pyrazin-1(2H)-one, and a mixture of (R) and (S)-7-(2-((2-chloro-4-fluorophenyl)amino)-5-methylpyrimidin-4-yl)-2-(1-(3-chlorophenyl)-2-hydroxyethyl)-3,4-dihydropyrrolo[1,2-a]pyrazin-1(2H)-one.

30. The compound of claim 29, and/or a pharmaceutically acceptable salt thereof, which is (S)-7-(2-((2-chloro-4-fluorophenyl)amino)-5-methylpyrimidin-4-yl)-2-(1-(3-chlorophenyl)-2-hydroxyethyl)-3,4-dihydropyrrolo[1,2-a]pyrazin-1(2H)-one.

31. A pharmaceutical composition, comprising a compound of claim 28, and/or a pharmaceutically acceptable salt, and a pharmaceutically acceptable carrier.

32. A method of treating cancer in a patient, comprising administering to the patient in recognized need of such treatment, an effective amount of a pharmaceutical composition comprising a compound of claim 28, and/or a pharmaceutically acceptable salt thereof, and a pharmaceutically acceptable carrier.

33. The method of claim 32, wherein the cancer is selected from colon cancer, gastric cancer, leukemia, lymphoma, melanoma, and pancreatic cancer.

* * * * *